(12) United States Patent
Blitz

(10) Patent No.: US 11,045,239 B2
(45) Date of Patent: Jun. 29, 2021

(54) ORTHOPEDIC BONE SCREW

(71) Applicant: Voom Medical Devices, Inc., New York, NY (US)

(72) Inventor: Neal Blitz, New York, NY (US)

(73) Assignee: Voom Medical Devices, Inc., New York, NY (US)

( * ) Notice: Subject to any disclaimer, the term of this patent is extended or adjusted under 35 U.S.C. 154(b) by 173 days.

(21) Appl. No.: 16/571,042

(22) Filed: Sep. 13, 2019

(65) Prior Publication Data

US 2020/0085477 A1    Mar. 19, 2020

Related U.S. Application Data

(60) Provisional application No. 62/731,540, filed on Sep. 14, 2018.

(51) Int. Cl.
*A61B 17/86* (2006.01)
*A61B 17/68* (2006.01)

(52) U.S. Cl.
CPC ...... *A61B 17/8615* (2013.01); *A61B 17/8625* (2013.01); *A61B 2017/681* (2013.01)

(58) Field of Classification Search
CPC .......................... A61B 17/8605; A61B 17/862
See application file for complete search history.

(56) References Cited

U.S. PATENT DOCUMENTS

| | | | |
|---|---|---|---|
| 5,443,509 A | 8/1995 | Boucher et al. | |
| 6,099,529 A | 8/2000 | Gertzman et al. | |
| 6,162,225 A | 12/2000 | Gertzman et al. | |
| 6,461,373 B2 | 10/2002 | Wyman et al. | |
| 6,953,463 B2 * | 10/2005 | West, Jr. | A61F 2/0811 606/326 |
| 7,083,647 B1 | 8/2006 | Sklar et al. | |
| 7,235,078 B2 | 6/2007 | West, Jr. | |
| RE42,526 E | 7/2011 | Reiser et al. | |
| 8,506,608 B2 | 8/2013 | Cerynik et al. | |
| 8,574,272 B2 | 11/2013 | Wallenstein et al. | |
| 8,608,785 B2 | 12/2013 | Reed et al. | |
| 8,636,785 B2 | 1/2014 | Hes et al. | |
| 8,968,374 B2 | 3/2015 | Hoof et al. | |
| D738,504 S | 9/2015 | Weiner et al. | |
| 9,271,775 B2 | 3/2016 | Lavi | |
| 9,724,139 B2 | 8/2017 | McCormick et al. | |
| 9,724,140 B2 | 8/2017 | McCormick | |
| 9,763,717 B2 | 9/2017 | Chiquillo Perez | |
| D801,796 S | 11/2017 | Sweeney et al. | |
| 2002/0052605 A1 | 5/2002 | Grooms et al. | |
| 2015/0182270 A1 | 7/2015 | Schwager et al. | |
| 2016/0015438 A1 | 1/2016 | Elleby et al. | |
| 2016/0143676 A1 | 5/2016 | Koay et al. | |

(Continued)

OTHER PUBLICATIONS

International Search Report and Written Opinion for PCT/US2019/051185, which is the PCT counterpart to U.S. Appl. No. 16/571,042.

*Primary Examiner* — Olivia C Chang
(74) *Attorney, Agent, or Firm* — Jonathan D. Spangler; Jay Bell

(57) ABSTRACT

The present disclosure describes a bone screw for use in orthopedic procedures. The bone screw includes a shank portion having a helical thread and a head portion also having a helical thread. The head portion has a reverse frustoconical shape, with the conical taper decreasing in the proximal direction.

20 Claims, 19 Drawing Sheets

(56) References Cited

U.S. PATENT DOCUMENTS

| | | |
|---|---|---|
| 2016/0354127 A1 | 12/2016 | Lundquist |
| 2017/0112555 A1 | 4/2017 | Wallenstein et al. |
| 2017/0189090 A1 | 7/2017 | Champagne et al. |
| 2017/0265875 A1* | 9/2017 | Granberry .......... A61B 17/1682 |
| 2018/0049881 A1 | 2/2018 | Austin et al. |
| 2018/0070995 A1 | 3/2018 | Kay et al. |
| 2018/0185076 A1 | 7/2018 | Zander et al. |

* cited by examiner

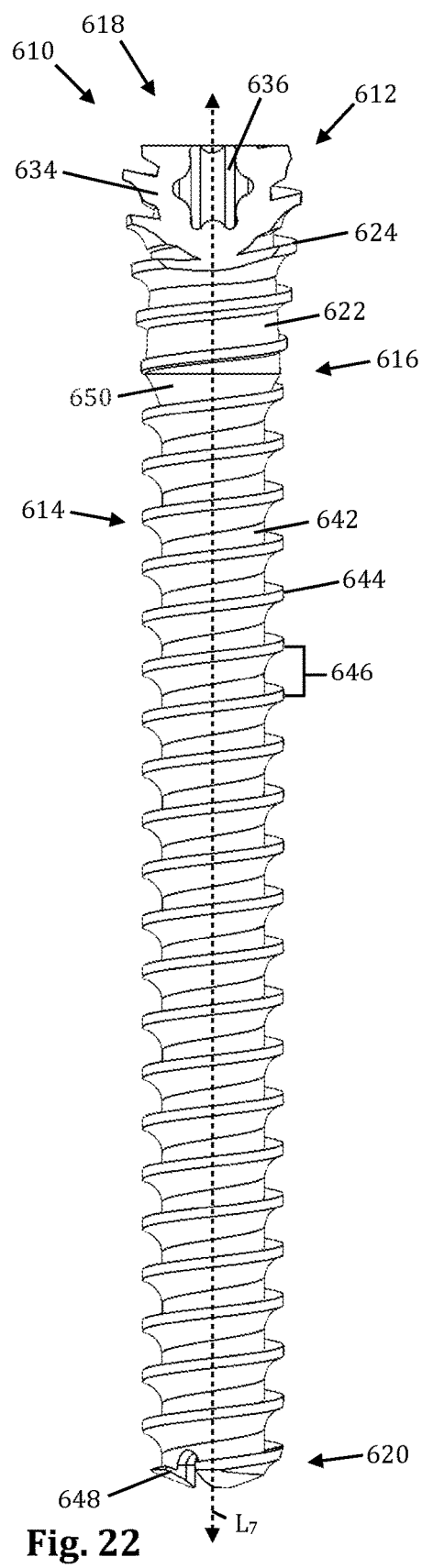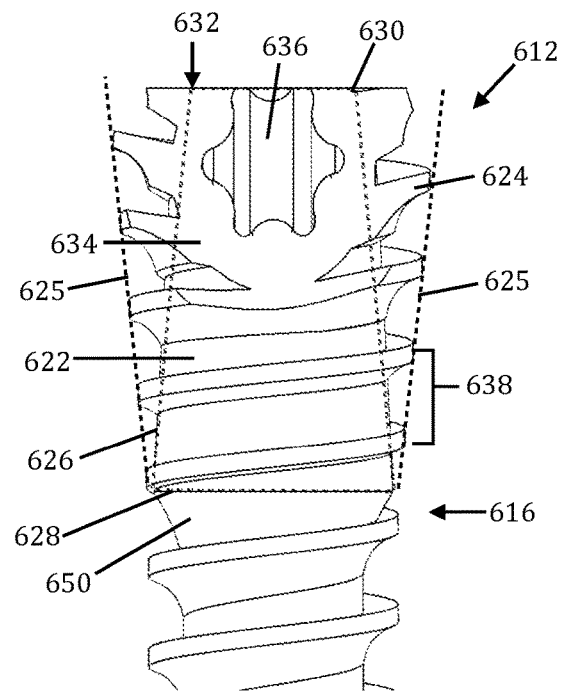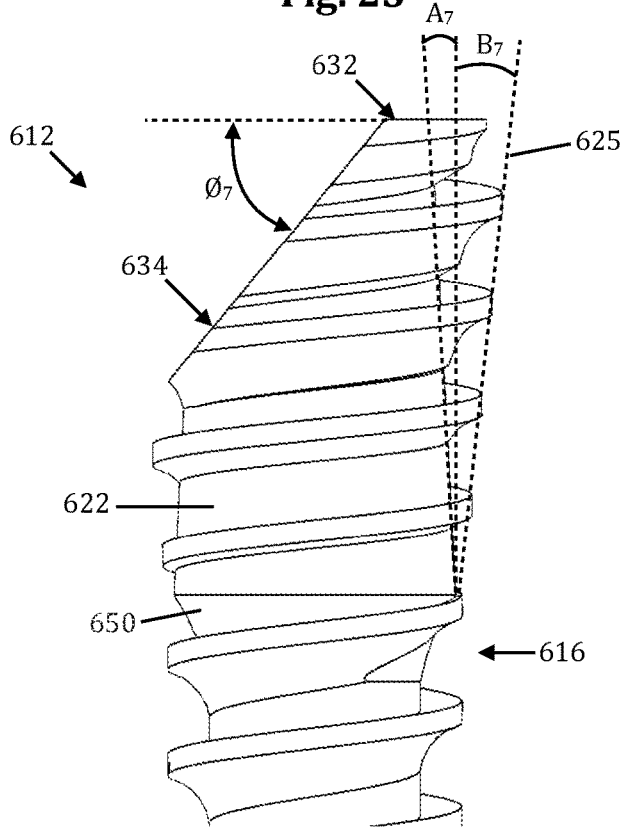
Fig. 22
Fig. 23
Fig. 24

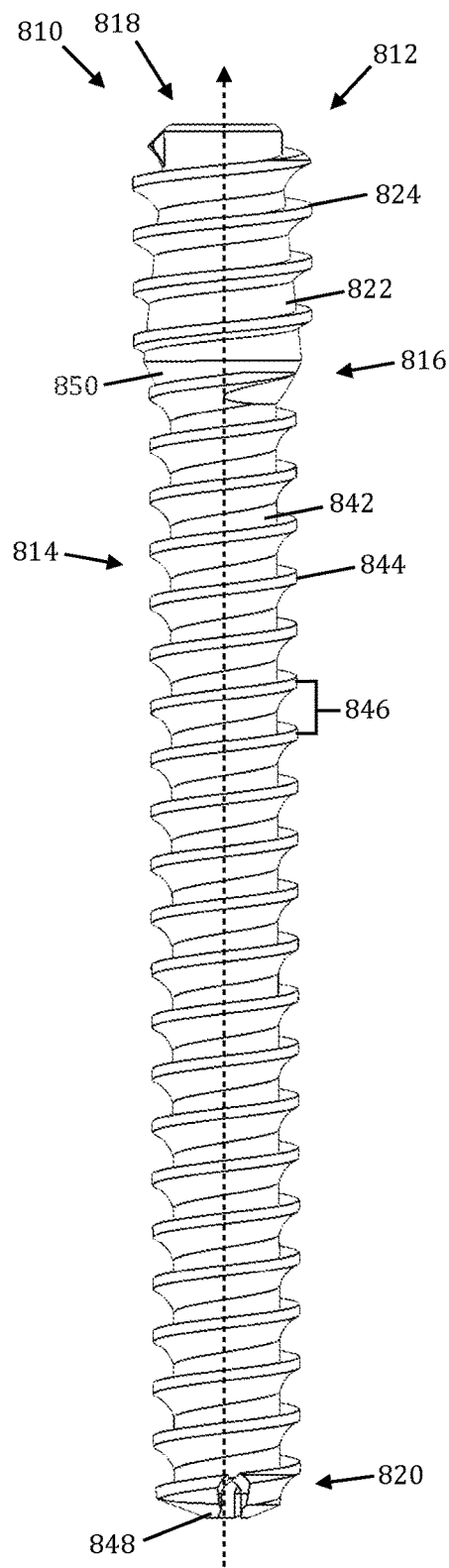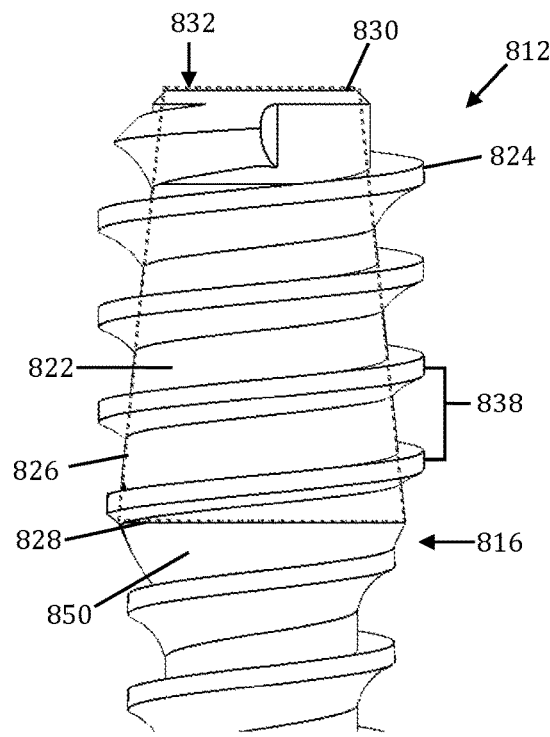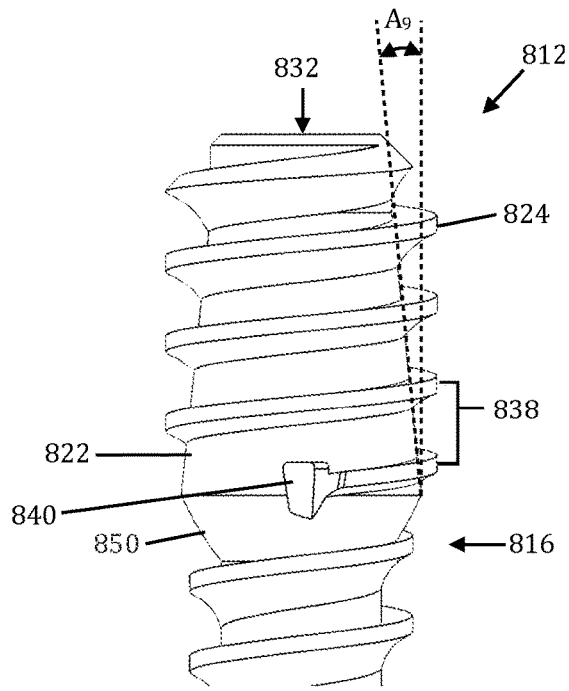
Fig. 28
Fig. 29
Fig. 30

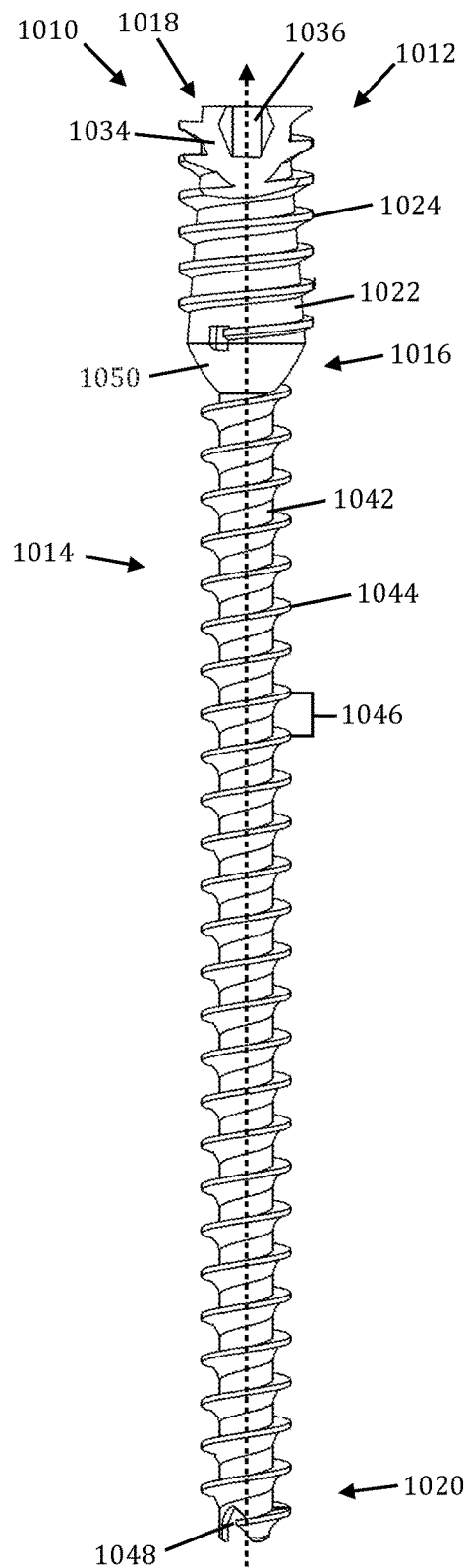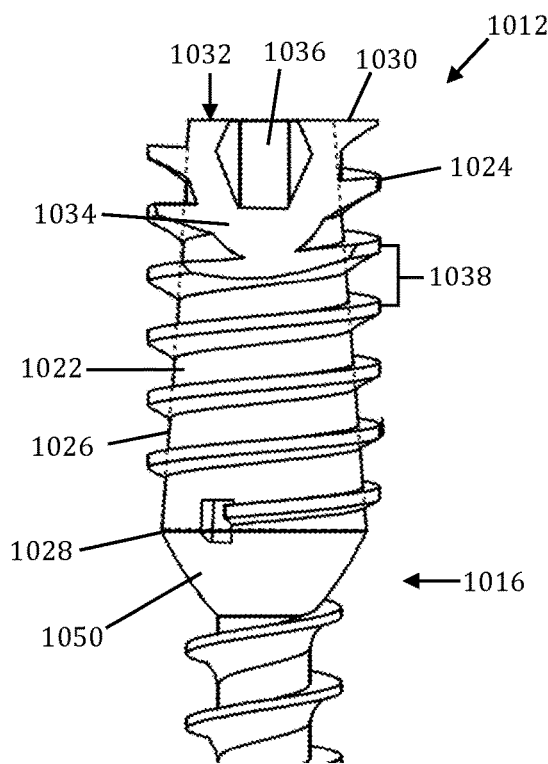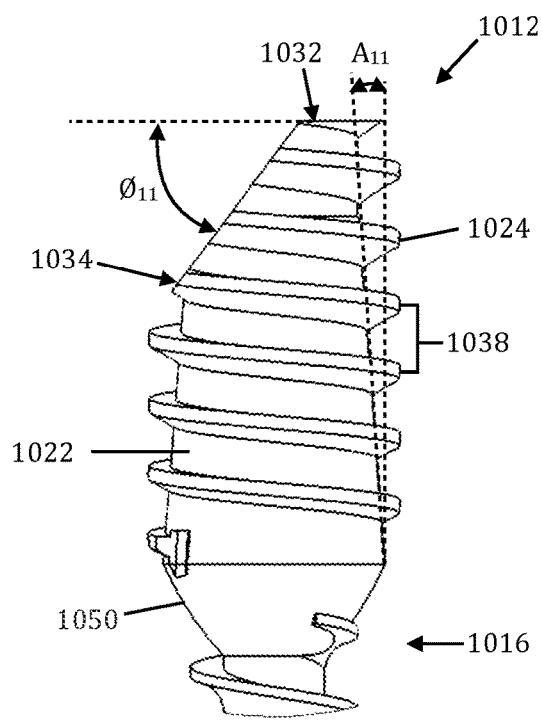
Fig. 34
Fig. 35
Fig. 36

ORTHOPEDIC BONE SCREW

CROSS-REFERENCES TO RELATED APPLICATIONS

The present application is a non-provisional application claiming the benefit of priority under 35 U.S.C. § 119(e) from commonly owned and U.S. Provisional Application Ser. No. 62/731,540 filed on Sep. 14, 2018 and entitled "ORTHOPEDIC BONE SCREW," the entire contents of which is hereby incorporated by reference into this disclosure as if set forth fully herein.

FIELD

The present disclosure relates generally to bone screws for use in orthopedic procedures, and more specifically to a bone screw having a frustoconical head with a decreasing taper in the proximal direction.

BACKGROUND

Bone screws typically have three main parts: head, shank, and thread. The head of most screws has a generally frustoconical shape—that is, resembling a frustum of a cone, which is formed by cutting off the tip of a cone with a cut perpendicular to the height, forming a lower base and an upper base that are circular and parallel, the lower base being the wider original base of the cone and the upper base being the narrower newly formed surface. The wider base of the frustum comprises the top (or proximal facing surface) of the screw, and is often provided with a drive feature (e.g. single slot for receiving a flathead screwdriver, crosshatch slot for receiving a Phillips-type screwdriver). The narrower base of the frustum typically transitions into the shank and may form a distinct neck region.

SUMMARY

The various examples of bone screws described herein are suitable in a variety of orthopedic procedures, including but not limited to small bone repair (e.g. surgical repair of bone fractures in the hand, wrist, ankle, and foot, including Bunionplasty® bunion surgery, etc.), and large bone repair (e.g. surgical repair of long bones in the arms and legs). The bone screws described herein may be provided in a variety of length and/or diameter (both major and minor) dimensions as needed. The bone screws described herein may be compression or compression-neutral. The bone screws described herein may also be configured for implantation at extreme angles without protruding from the bone.

In some embodiments, the orthopedic bone screw described herein includes a head, a shank, and a neck positioned between the head and shank. The bone screw further comprises a proximal end and a distal end. The head is positioned at/near the proximal end of the bone screw, and the shank extends axially along a longitudinal axis from the neck to the distal end of the bone screw. The head comprises a curved lateral surface and a helical thread disposed around the curved lateral surface.

In some embodiments, the head has a generally frustoconical cross-sectional shape, however unlike typical prior art bone screws in which the wide base of the frustum forms the proximal-most (or top) surface of the screw, in the bone screw of the present disclosure the narrow base of the frustum forms the proximal-most (or top) surface of the bone screw. This orientation may be referred to herein as "reverse conical" or "reverse frustoconical" to indicate that the orientation of frustoconical shape is flipped vertically relative to a typical prior art bone screw.

In some embodiments, the curved lateral surface is tapered in the proximal direction from the wide base to the narrow base. The taper angle may be within the range of 4-15° measured relative to the longitudinal axis (and its parallels). The taper angle of the curved lateral surface may also be characterized in terms of the inclusive angle of the cone defining the frustoconical shape of the head. In such a characterization, the inclusive angle may be within a range of 8-30°.

In some embodiments, the head may have a minor diameter within the range of 1.75 mm to 9.0 mm at the wide base, and a major diameter within the range of 2.0 mm to 10.0 mm. The first minor diameter is less than the major diameter (of the helical thread).

In some embodiments, the head may include an angled surface (also "chamfer" or "bevel") and a driver recess. The angled surface is formed between the top surface and the lateral surface. The top surface has a width dimension that is greater than zero as measured along a diameter of the head, ensuring that the angled surface does not extend completely across the top of the screw.

In some embodiments, the head may include an angled surface/chamfer/bevel formed between the top surface and the lateral surface such that the width dimension of the top surface is approximately zero (e.g., the angled surface extends completely across the top of the screw).

In some embodiments, the angled surface may have a bevel angle within the range of 1-60° measured from the plane of the top surface, which is generally perpendicular to the longitudinal axis. The angled surface reduces/eliminates the amount of screw material that may extend beyond the edge of a bone structure when the bone screw is implanted at an angle relative to the bone structure.

In some embodiments, the driver recess is formed into the top surface and angled surface along the longitudinal axis, and may have any shape suitable to receive a driver (e.g. flathead, Phillips-type, hexalobe, torx, etc.).

In some embodiments, the helical thread of the head may have a pitch (e.g. the distance between adjacent threads at any one location) within the range of 0.5 mm to 2.5 mm.

In some embodiments, the helical thread of the head may have a variable pitch.

In some embodiments, the bone screw may be compression-neutral. In this embodiment, the helical thread of the head may have the same pitch as the helical thread of the shank, or alternatively the helical thread of the head may have a pitch that is an even multiple (e.g. 2×) of the pitch of the helical thread on the shank.

In some embodiments, the bone screw may be a compression screw. In this embodiment, the helical thread of the head may have a different pitch than the pitch of the helical thread on the shank, with said head pitch being not an even multiple of the shank pitch.

In some embodiments, the head may include a cutting flute formed at the distal end of the helical thread, which acts to clear out bone material as the screw is driven into bone, to ease the transition from the shank to the head.

In some embodiments, the helical thread of the head has a major diameter that remains constant.

In some embodiments, the helical thread of the head has a proximally-oriented outward taper so that the major diameter at the proximal end is greater than the major diameter near the neck, and as a result, the surface area of the helical thread in contact with bone increases in a distal to proximal direction, enhancing the purchase of the screw into the bone.

In some embodiments, the helical thread of the head has a proximally-oriented inward taper so that the major diameter at the proximal end is less than the major diameter near the neck.

In some embodiments, the inward taper of the helical thread has a taper angle that is identical to the taper angle of the curved lateral surface.

In some embodiments, the shank is cylindrical in shape, and extends from a proximal end adjacent the neck to the distal end of the bone screw. The shank comprises a curved lateral surface and a helical thread disposed around the curved lateral surface.

In some embodiments, the shank may have a minor diameter within the range of 1.0 mm to 7.5 mm and a major diameter within the range of 1.5 mm to 8 mm. Preferably, the major diameter of the shank is less than the major diameter of the head.

In some embodiments, the helical thread of the shank may have a pitch within the range of 0.5 mm to 2.5 mm.

In some embodiments, the shank may have a pair of helical threads, each having a pitch within the range of 0.5 mm to 5.0 mm.

In some embodiments, the shank includes one or more cutting flutes disposed at the distal end. The cutting flute acts to clear out bone material as the screw is driven into bone, which obviates the need for drilling a pilot hole during the surgical procedure.

In some embodiments, the bone screw includes one or more reverse cutting flutes to clear out bone material as the screw is removed from bone.

In some embodiments, the neck comprises a curved lateral surface that is tapered in the distal direction, to provide a smooth transition between the reverse conical head and the shank.

In some embodiments, the bone screw is cannulated, including a central lumen extending axially through the entirety of the screw. The central lumen is sized and configured to receive a guide wire (e.g. K-wire) therethrough to guide the bone screw to the correct implantation location.

It is important to note that any element or feature shown and described herein with respect to any particular example embodiment may be used in combination with any other feature(s) or element(s) shown and described with respect to other example embodiments without limitation.

BRIEF DESCRIPTION OF THE DRAWINGS

Many advantages of the present disclosure will be apparent to those skilled in the art with a reading of this specification in conjunction with the attached drawings, wherein like reference numerals are applied to like elements and wherein:

FIG. 22 is a front plan view of a seventh example of a bone screw according to an embodiment of the disclosure;

FIG. 23 is a front plan view of the head region of the bone screw of FIG. 22;

FIG. 24 is a side plan view of the head region of FIG. 23;

FIG. 28 is a front plan view of a ninth example of a bone screw according to an embodiment of the disclosure;

FIG. 29 is a front plan view of the head region of the bone screw of FIG. 28;

FIG. 30 is a side plan view of the head region of FIG. 29;

FIG. 34 is a front plan view of an eleventh example of a bone screw according to an embodiment of the disclosure;

FIG. 35 is a front plan view of the head region of the bone screw of FIG. 34;

FIG. 36 is a side plan view of the head region of FIG. 34;

DETAILED DESCRIPTION OF A PREFERRED EMBODIMENT

Figure 1:
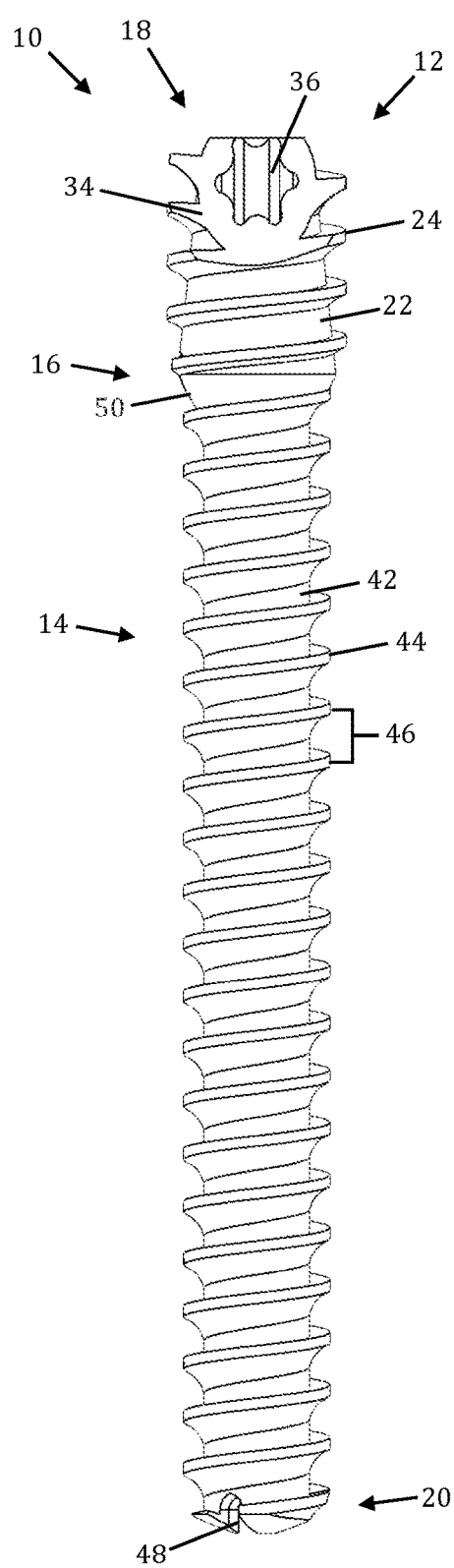
FIG. 1 is a front plan view of a first example of a bone screw according to an embodiment of the disclosure.
Figure 2:
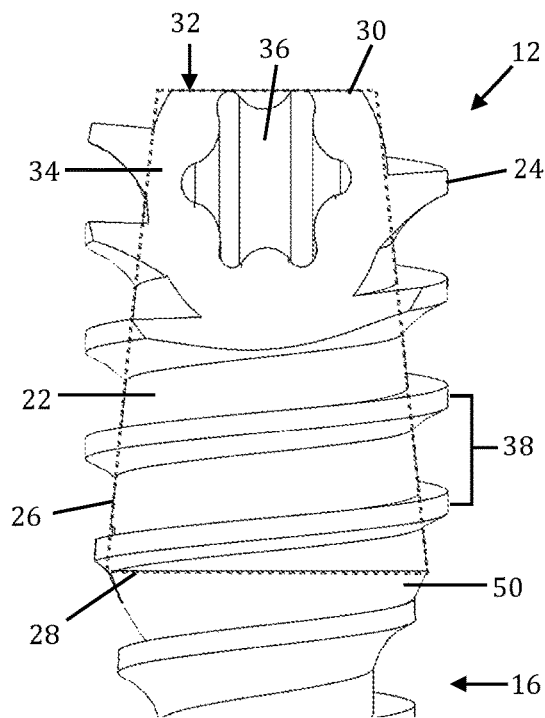
FIG. 2 is a front plan view of the head region of the bone screw of FIG. 1.
Figure 3:
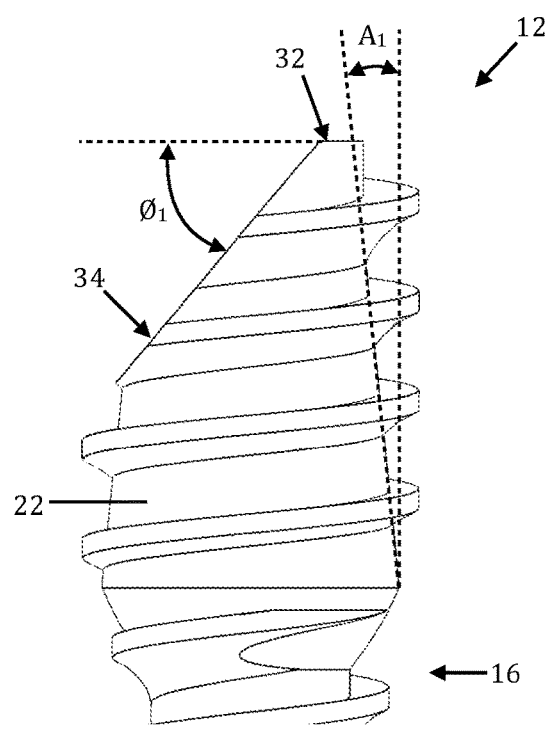
FIG. 3 is a side plan view of the head region of FIG. 2.
Figure 4:
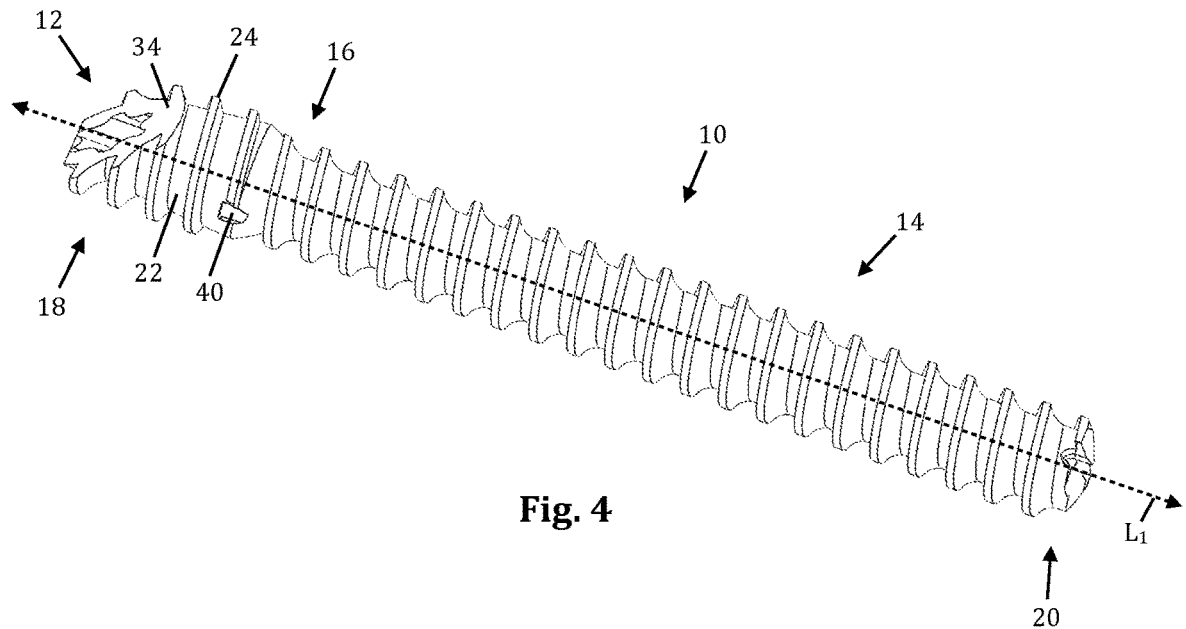
FIG. 4 is a perspective view of the bone screw of FIG. 1.
Figure 5:
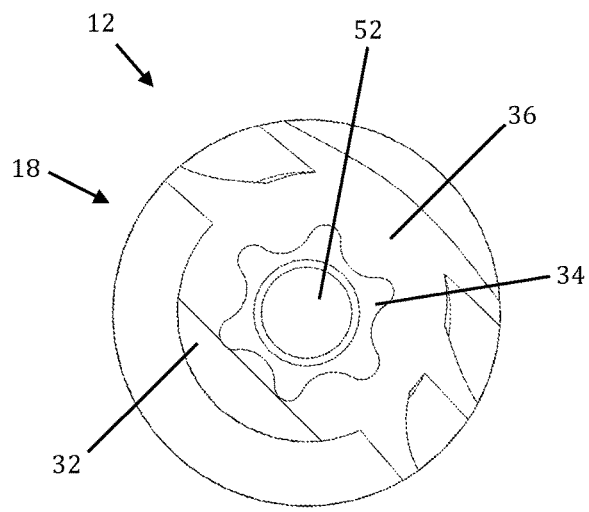
FIG. 5 is a top plan view of the bone screw of FIG. 1.
Figure 6:
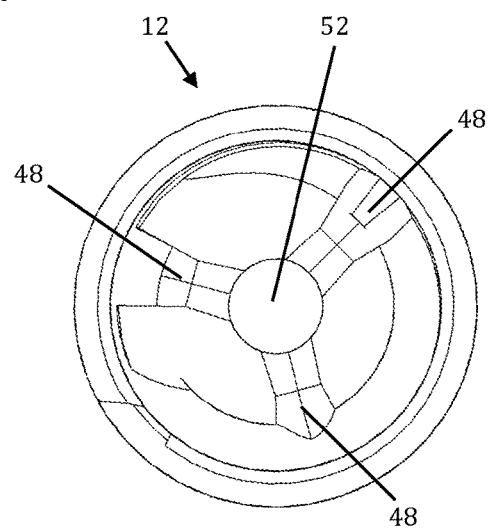
FIG. 6 is a bottom plan view of the bone screw of FIG. 1.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The bone screw and related methods disclosed herein boasts a variety of inventive features and components that warrant patent protection, both individually and in combination.

The various examples of bone screws described herein are suitable in a variety of orthopedic procedures, including but not limited to small bone repair (e.g. surgical repair of bone fractures in the hand, wrist, ankle, and foot, including Bunionplasty® bunion surgery, talus neck fracture repair, etc.), and large bone repair (e.g. surgical repair of long bones in the arms and legs). The bone screws described herein may be provided in a variety of length and/or diameter (both major and minor) dimensions as needed. The bone screws described herein may be compression or compression-neutral.

FIGS. 1-6 illustrate an example of a bone screw 10 according to one embodiment of the disclosure. By way of example, the bone screw 10 includes a head 12, a shank 14, and a neck 16 positioned between the head 12 and shank 14. The bone screw 10 further comprises a proximal end 18 and a distal end 20. The head 12 is positioned at/near the proximal end 18 of the bone screw 10, and the shank 14 extends axially along a longitudinal axis $L_1$ (also "vertical axis") from the neck 16 to the distal end 20 of the bone screw 10. The head 12 comprises a curved lateral surface 22 and a helical thread 24 disposed around the curved lateral surface 22. The head 12 has a generally frustoconical cross-sectional shape 26, however unlike typical prior art bone screws in which the wide base 28 of the frustum forms the proximal-most (or top) surface of the screw, in the instant example the narrow base 30 of the frustum forms the proximal-most (or top) surface 32 of the bone screw 10. This orientation may be referred to herein as "reverse conical" or "reverse frustoconical" to indicate that the orientation of frustoconical shape is flipped vertically relative to a typical prior art bone screw. The curved lateral surface 22 is tapered in the proximal direction from the wide base 28 to the narrow base 30. By way of example, the curved lateral surface 22 is tapered at an angle $A_1$ of 5.9° relative to the longitudinal axis $L_1$ (resulting in the cone defining the shape of the head having an included angle of 11.8°), however the angle $A_1$ may be within the range of 4-15° (8-30° inclusive angle) without departing from the scope of the disclosure.

The head 12 may have a minor diameter within the range of 1.75 mm to 9.0 mm at the wide base 28. The head 12 has a major diameter (e.g. the outer diameter of the helical thread 24) within the range of 2.0 mm to 10.0 mm. The first minor diameter is less than the major diameter (of the helical thread 24). By way of example, the head 12 of the bone screw 10 shown in FIGS. 1-4 has a minor diameter of approximately 4.5 mm at the wide base 28 and a major diameter of approximately 5.0 mm. As a result of the frustoconical shape, the head 12 has a minor diameter that increases in a proximal to distal direction. The major diameter remains constant, and as a result the thread surface area in contact with bone increases in a distal to proximal direction, enhancing the purchase of the screw into the bone.

The head 12 further includes an angled surface 34 (also "chamfer" or "bevel") and a driver recess 36. The angled surface 34 is formed between the top surface 32 and the lateral surface 22. The top surface 32 has a width dimension that is greater than zero as measured along a diameter of the head, ensuring that the angled surface 34 does not extend completely across the top of the screw 10. In the instant example, the top surface 32 has a width dimension of 0.65 mm, however the width dimension may be more or less depending upon the overall size of the bone screw 10. By way of example, the angled surface 34 may have a bevel angle $Ø_1$ within the range of 1-60° measured from the plane of the top surface 32, which is generally perpendicular to the longitudinal axis $L_1$. By way of example, the bevel angle $Ø_1$ of the bone screw 10 shown in FIGS. 1-6 is 50°. The angled surface 34 is positioned generally parallel to and flush with an exterior surface of the bone forming part of the anatomical target site when the head is implanted during use to thereby reduce or eliminate a degree to which the head will extend beyond the exterior surface of the bone when the bone screw 10 is implanted at an angle relative to the bone structure. The driver recess 36 is formed into the top surface 32 and angled surface 34 along the longitudinal axis $L_1$, and may have any shape suitable to receive a driver (e.g. flathead, Phillips-type, hexalobe, torx, etc.).

The helical thread 24 may have a pitch 38 (e.g. the distance between adjacent threads at any one location) within the range of 0.5 mm to 2.5 mm. By way of example, the helical thread 24 of the present example has a 1.5 mm pitch. The head 12 may further include a cutting flute 40 formed at the distal end of the helical thread 24, which acts to clear out bone material as the screw 10 is driven into bone, to ease the transition from the shank 14 to the head 12.

By way of example, the shank 14 is cylindrical in shape, and extends from a proximal end adjacent the neck 16 to the distal end 20 of the bone screw 10. The shank 14 comprises a curved lateral surface 42 and a helical thread 44 disposed around the curved lateral surface 42. The shank 14 may have a minor diameter within the range of 1.0 mm to 7.5 mm and a major diameter within the range of 1.5 mm to 8 mm. Preferably, the major diameter of the shank 14 is less than the major diameter of the head 12. In the example shown and described herein, the shank 14 has a minor diameter of 3 mm and a major diameter of approximately 4 mm. The helical thread 44 may have a pitch 46 within the range of 0.5 mm to 2.5 mm. By way of example, the helical thread 44 of the present example has a 1.5 mm pitch, which is the same as the pitch of the helical thread 24 of the head 12. Because the head 12 and shank 14 have the same pitch, the bone screw 10 is compression neutral. The shank 14 further includes one or more cutting flutes 48 disposed at the distal end 20. The cutting flute 48 acts to clear out bone material as the screw 10 is driven into bone, which obviates the need for drilling a pilot hole during the surgical procedure.

The neck 16 comprises a curved lateral surface 50 that is tapered in the distal direction, to provide a smooth transition between the reverse conical head 12 and the shank 14.

By way of example, the bone screw 10 may be cannulated, further including a central lumen 52 extending axially through the entirety of the screw 10. The central lumen 52 is sized and configured to receive a guide wire (e.g. K-wire) therethrough to guide the bone screw 10 to the correct implantation location.

Figure 7:
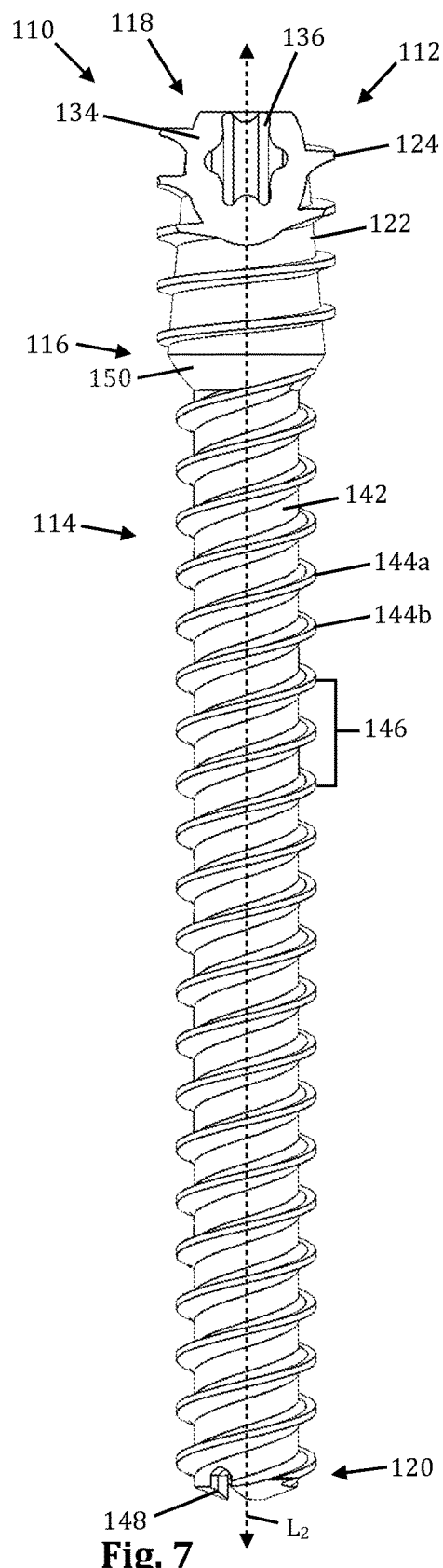
FIG. 7 is a front plan view of a second example of a bone screw according to an embodiment of the disclosure.
Figure 8:
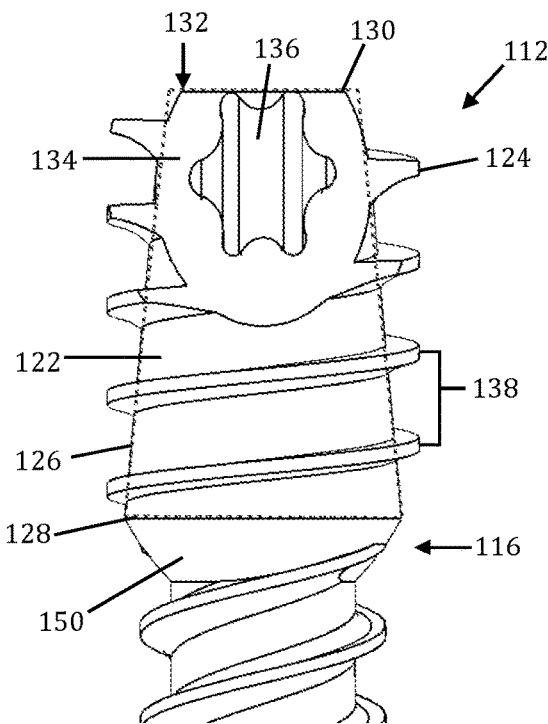
FIG. 8 is a front plan view of the head region of the bone screw of FIG. 7.
Figure 9:
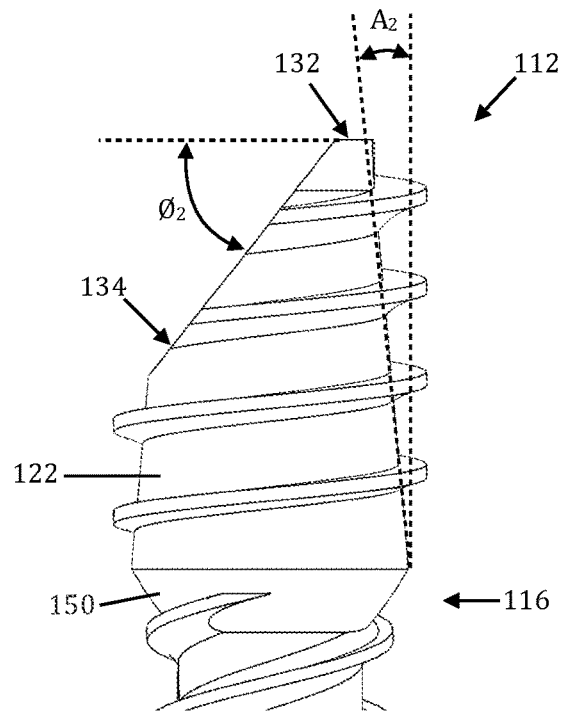
FIG. 9 is a side plan view of the head region of FIG. 8.

FIGS. 7-9 illustrate an example of a bone screw 110 according to another embodiment of the disclosure. By way of example, the bone screw 110 includes a head 112, a shank 114, and a neck 116 positioned between the head 112 and shank 114. The bone screw 110 further comprises a proximal end 118 and a distal end 120. The head 112 is positioned at/near the proximal end 118 of the bone screw 110, and the shank 114 extends axially along a longitudinal axis $L_2$ (also "vertical axis") from the neck 116 to the distal end 120 of the bone screw 110. The head 112 comprises a curved lateral surface 122 and a helical thread 124 disposed around the curved lateral surface 122. The head 112 has a reverse frustoconical cross-sectional shape 126 as described above with respect to bone screw 10. The curved lateral surface 122 is tapered in the proximal direction from the wide base 128 to the narrow base 130. By way of example, the curved lateral surface 122 is tapered at an angle $A_2$ of 5.9° relative to the longitudinal axis $L_2$ (resulting in the cone defining the shape of the head having an included angle of 11.8°), however the angle $A_2$ may be within the range of 4-15° (8-30° inclusive angle) without departing from the scope of the disclosure.

The head 112 may have a minor diameter within the range of 1.75 mm to 9.0 mm at the wide base 128. The head 112 has a major diameter within the range of 2.0 mm to 10.0 mm. The first minor diameter is less than the major diameter (of the helical thread 124). By way of example, the head 112 of the bone screw 110 shown in FIGS. 7-9 has a minor diameter of approximately 4.5 mm at the wide base 128 and a major diameter of approximately 5.0 mm. As a result of the frustoconical shape, the head 112 has a minor diameter that increases in a proximal to distal direction. The major diameter remains constant, and as a result the thread surface area in contact with bone increases in a distal to proximal direction, enhancing the purchase of the screw into the bone.

The head 112 further includes an angled surface 134 (also "chamfer" or "bevel") and a driver recess 136. The angled surface 134 is formed between the top surface 132 and the lateral surface 122. The top surface 132 has a width dimension that is greater than zero as measured along a diameter of the head, ensuring that the angled surface 134 does not extend completely across the top of the screw 110. In the instant example, the top surface 132 has a width dimension of 0.65 mm, however the width dimension may be more or less depending upon the overall size of the bone screw 110. By way of example, the angled surface 134 may have a bevel angle $Ø_2$ within the range of 1-60° measured from the plane of the top surface 132, which is generally perpendicular to the longitudinal axis $L_2$. By way of example, the bevel angle $Ø_2$ of the bone screw 110 shown in FIGS. 7-9 is 50°. The angled surface 134 is positioned generally parallel to and flush with an exterior surface of the bone forming part of the anatomical target site when the head is implanted during use to thereby reduce or eliminate a degree to which the head will extend beyond the exterior surface of the bone when the bone screw 110 is implanted at an angle relative to the bone structure. The driver recess 136 is formed into the top surface 132 and angled surface 134 along the longitudinal axis $L_2$, and may have any shape suitable to receive a driver (e.g. flathead, Phillips-type, hexalobe, torx, etc.). The helical thread 124 may have a pitch 138 within the range of 0.5 mm to 2.5 mm. By way of example, the helical thread 124 of the present example has a 1.5 mm pitch.

By way of example, the shank 114 is cylindrical in shape, and extends from a proximal end adjacent the neck 116 to the distal end 120 of the bone screw 110. The shank 114 comprises a curved lateral surface 142 and a pair of helical threads 144a, 144b disposed around the curved lateral surface 142. The shank 114 may have a minor diameter within the range of 1.0 mm to 7.5 mm and a major diameter within the range of 1.5 mm to 8 mm. Preferably, the major diameter of the shank 114 is less than the major diameter of the head 112. In the example shown and described herein, the shank 114 has a minor diameter of 3 mm and a major diameter of approximately 4 mm. The helical threads 144a, 144b may have a pitch 146 within the range of 0.5 mm to 5.0 mm. By way of example, the helical threads 144a, 144b of the present example each have a 3.0 mm pitch (e.g. distance between adjacent threads of the same helix), however there are two helical threads 144a, 144b that are spaced evenly apart, making the effective pitch of the bone screw 110 1.5 mm which is the same as the pitch of the helical thread 124 of the head 112. Because the bone screw 110 uses a double helix configuration in the shank thread, the bone screw 110 is capable of being driven into the target bone at a rate approximately twice as fast as with a bone screw having a true pitch of 1.5 mm. Because the head 112 and shank 114 have the same pitch (or effective pitch), the bone screw 110 is compression neutral. The shank 114 further includes one or more cutting flutes 148 disposed at the distal end 120. The cutting flute 148 acts to clear out bone material as the screw 110 is driven into bone, which obviates the need for drilling a pilot hole during the surgical procedure.

The neck 116 comprises a curved lateral surface 150 that is tapered in the distal direction, to provide a smooth transition between the reverse conical head 112 and the shank 114.

The bone screw 110 further includes a central lumen extending axially through the entirety of the screw 110 similar to the central lumen 52 shown and described above with respect to the bone screw 10. The central lumen 152 is sized and configured to receive a guide wire (e.g. K-wire) therethrough to guide the bone screw 110 to the correct implantation location.

Figure 10:
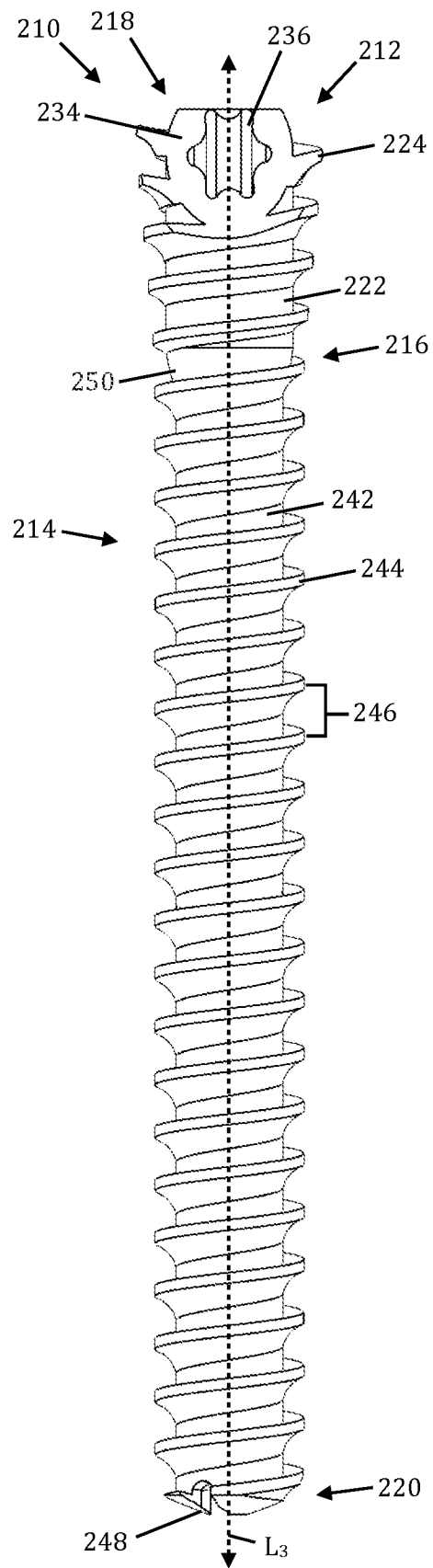
FIG. 10 is a front plan view of a third example of a bone screw according to an embodiment of the disclosure.
Figure 11:
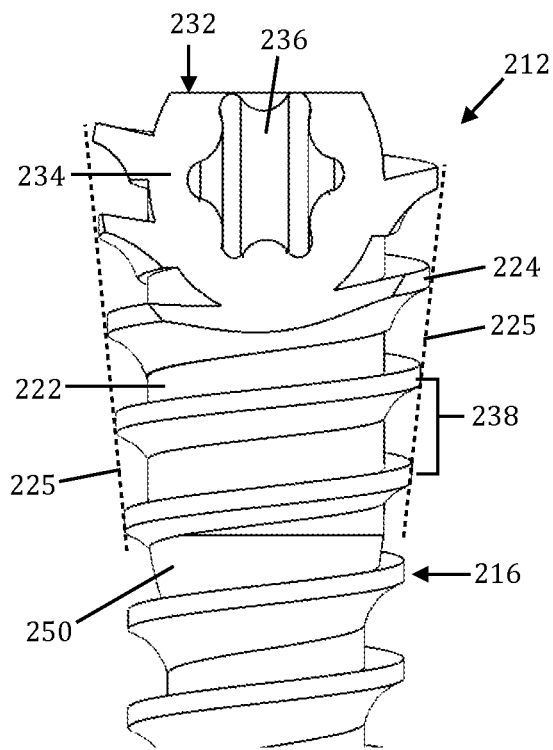
FIG. 11 is a front plan view of the head region of the bone screw of FIG. 10.
Figure 12:
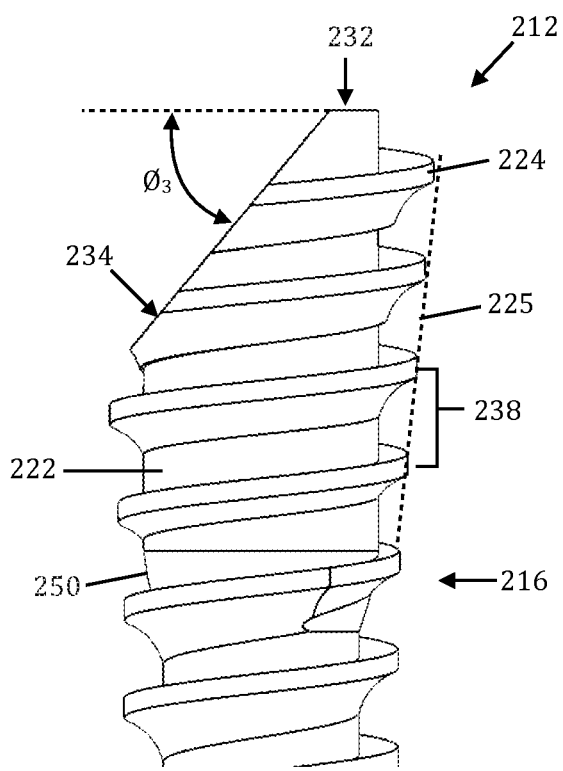
FIG. 12 is a side plan view of the head region of FIG. 11.

FIGS. 10-12 illustrate an example of a bone screw 210 according to another embodiment of the disclosure. By way of example, the bone screw 210 includes a head 212, a shank 214, and a neck 216 positioned between the head 212 and shank 214. The bone screw 210 further comprises a proximal end 218 and a distal end 220. The head 212 is positioned at/near the proximal end 218 of the bone screw 210, and the shank 214 extends axially along a longitudinal axis $L_3$ (also "vertical axis") from the neck 216 to the distal end 220 of the bone screw 210. The head 212 comprises a curved lateral surface 222 and a helical thread 224 disposed around the curved lateral surface 222. The head 212 has a generally cylindrical shape. The helical thread 224 has a major diameter that increases in the distal to proximal direction. As a result the thread surface area in contact with bone increases in a distal to proximal direction, enhancing the purchase of the screw into the bone.

The head 212 further includes an angled surface 234 (also "chamfer" or "bevel") and a driver recess 236. The angled surface 234 is formed between the top surface 232 and the lateral surface 222. The top surface 232 has a width dimension that is greater than zero as measured along a diameter of the head, ensuring that the angled surface 234 does not extend completely across the top of the screw 210. In the instant example, the top surface 232 has a width dimension of 0.65 mm, however the width dimension may be more or less depending upon the overall size of the bone screw 210. By way of example, the angled surface 234 may have a bevel angle $\varnothing_3$ within the range of 1-60° measured from the plane of the top surface 232, which is generally perpendicular to the longitudinal axis $L_3$. By way of example, the bevel angle $\varnothing_3$ of the bone screw 210 shown in FIGS. 10-12 is 50°. The angled surface 234 is positioned generally parallel to and flush with an exterior surface of the bone forming part of the anatomical target site when the head is implanted during use to thereby reduce or eliminate a degree to which the head will extend beyond the exterior surface of the bone when the bone screw 210 is implanted at an angle relative to the bone structure. The driver recess 236 is formed into the top surface 232 and angled surface 234 along the longitudinal axis $L_3$, and may have any shape suitable to receive a driver (e.g. flathead, Phillips-type, hexalobe, torx, etc.).

The helical thread 224 may have a pitch 238 (e.g. the distance between adjacent threads at any one location) within the range of 0.5 mm to 2.5 mm. By way of example, the helical thread 224 of the present example has a 1.5 mm pitch. The thread 224 has a 10° (for example) proximally-oriented outward taper 225 so that the major diameter at the proximal end 218 is greater than the major diameter near the neck 216, and as a result, the surface area of the helical thread 224 in contact with bone increases in a distal to proximal direction, enhancing the purchase of the screw into the bone.

By way of example, the shank 214 is cylindrical in shape, and extends from a proximal end adjacent the neck 216 to the distal end 220 of the bone screw 210. The shank 214 comprises a curved lateral surface 242 and a helical thread 244 disposed around the curved lateral surface 242. The shank 214 may have a minor diameter within the range of 1.0 mm to 7.5 mm and a major diameter within the range of 1.5 mm to 8 mm. Preferably, the major diameter of the shank 214 is less than the major diameter of the head 212. In the example shown and described herein, the shank 214 has a minor diameter of 3 mm and a major diameter of approximately 4 mm. The helical thread 244 may have a pitch 246 within the range of 0.5 mm to 2.5 mm. By way of example, the helical thread 244 of the present example has a 1.5 mm pitch, which is the same as the pitch of the helical thread 224 of the head 212. Because the head 212 and shank 214 have the same pitch, the bone screw 210 is compression neutral. The shank 214 further includes one or more cutting flutes 248 disposed at the distal end 220. The cutting flute 248 acts to clear out bone material as the screw 210 is driven into bone, which obviates the need for drilling a pilot hole during the surgical procedure.

The neck 216 comprises a curved lateral surface 250 that is tapered in the distal direction, to provide a smooth transition between the reverse conical head 212 and the shank 214.

The bone screw 210 further includes a central lumen extending axially through the entirety of the screw 210, identical to the central lumen 52 shown and described above with respect to bone screw 10. The central lumen is sized and configured to receive a guide wire (e.g. K-wire) therethrough to guide the bone screw 210 to the correct implantation location.

Figure 13:
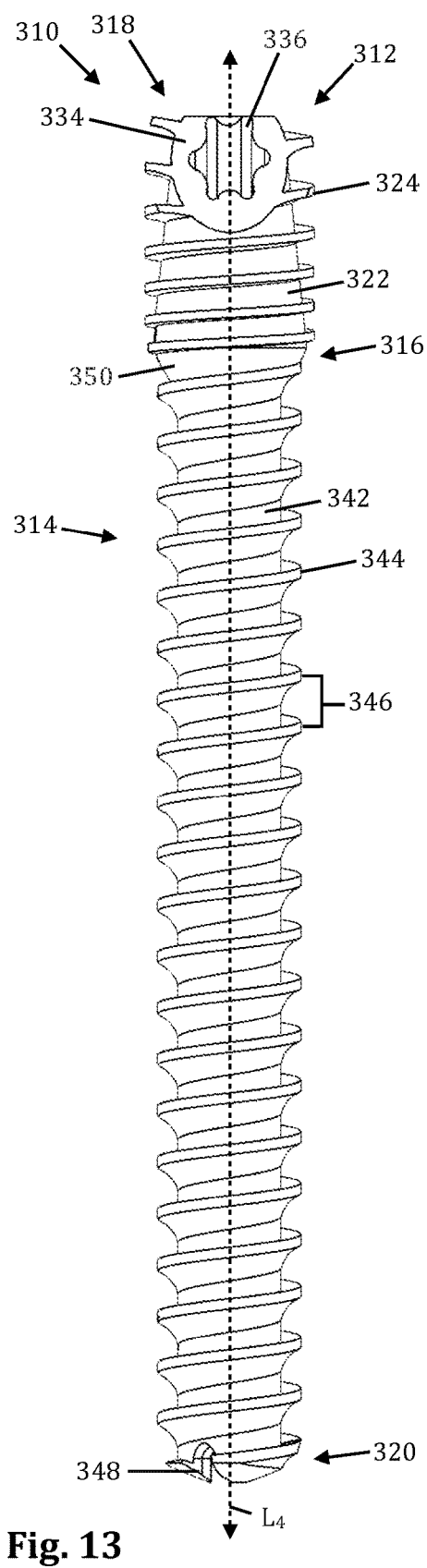
FIG. 13 is a front plan view of a fourth example of a bone screw according to an embodiment of the disclosure.
Figure 14:
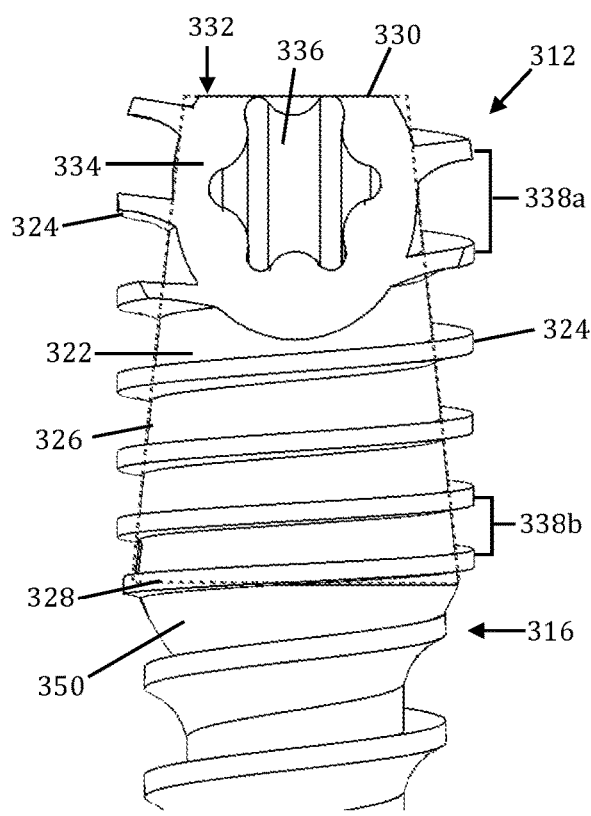
FIG. 14 is a front plan view of the head region of the bone screw of FIG. 13.
Figure 15:
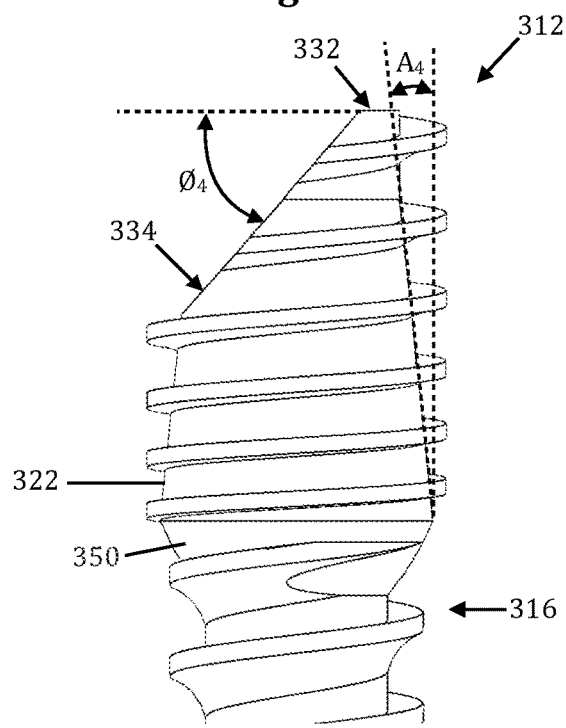
FIG. 15 is a side plan view of the head region of FIG. 14.

FIGS. 13-15 illustrate an example of a bone screw 310 according to another embodiment of the disclosure. By way of example, the bone screw 310 includes a head 312, a shank 314, and a neck 316 positioned between the head 312 and shank 314. The bone screw 310 further comprises a proximal end 318 and a distal end 320. The head 312 is positioned at/near the proximal end 318 of the bone screw 310, and the shank 314 extends axially along a longitudinal axis $L_4$ (also "vertical axis") from the neck 316 to the distal end 320 of the bone screw 310. The head 312 comprises a curved lateral surface 322 and a helical thread 324 disposed around the curved lateral surface 322. The head 312 has a reverse frustoconical cross-sectional shape 326 as described above with respect to bone screw 10. The curved lateral surface 322 is tapered in the proximal direction from the wide base 328 to the narrow base 330. By way of example, the curved lateral surface 322 is tapered at an angle $A_4$ of 5.9° relative to the longitudinal axis $L_4$ (resulting in the cone defining the shape of the head having an included angle of 11.8°), however the angle $A_4$ may be within the range of 4-15° (8-30° inclusive angle) without departing from the scope of the disclosure.

The head 312 may have a minor diameter within the range of 1.75 mm to 9.0 mm at the wide base 328. The head 312 has a major diameter within the range of 2.0 mm to 10.0 mm. The first minor diameter is less than the major diameter (of the helical thread 324). By way of example, the head 312 of the bone screw 310 shown in FIGS. 13-15 has a minor diameter of approximately 4.5 mm at the wide base 328 and a major diameter of approximately 5.0 mm. As a result of the frustoconical shape, the head 312 has a minor diameter that increases in a proximal to distal direction. The major diameter remains constant, and as a result the thread surface area in contact with bone increases in a distal to proximal direction, enhancing the purchase of the screw into the bone.

The head 312 further includes an angled surface 334 (also "chamfer" or "bevel") and a driver recess 336. The angled surface 334 is formed between the top surface 332 and the lateral surface 322. The top surface 332 has a width dimension that is greater than zero as measured along a diameter of the head, ensuring that the angled surface 334 does not extend completely across the top of the screw 310. In the instant example, the top surface 332 has a width dimension of 0.65 mm, however the width dimension may be more or less depending upon the overall size of the bone screw 310. By way of example, the angled surface 334 may have a bevel angle $\varnothing_4$ within the range of 1-60° measured from the plane of the top surface 332, which is generally perpendicular to the longitudinal axis $L_1$. By way of example, the bevel angle $\varnothing_4$ of the bone screw 310 shown in FIGS. 13-15 is 50°. The angled surface 334 is positioned generally parallel to and flush with an exterior surface of the bone forming part of the anatomical target site when the head is implanted during use to thereby reduce or eliminate a degree to which the head will extend beyond the exterior surface of the bone when the bone screw 310 is implanted at an angle relative to the bone structure. The driver recess 336 is formed into the top surface 332 along the longitudinal axis $L_4$, and may have any shape suitable to receive a driver (e.g. flathead, Phillips-type, hexalobe, torx, etc.).

The helical thread 324 may have a variable pitch within the range of 0.5 mm to 2.5 mm at the distal end of the head 312 and a range of 1.0 mm to 5.0 mm at the proximal end of the head. By way of example, the helical thread 324 of the present example has a pitch 338a of 1.5 mm at the proximal end of the head 312 that gradually decreases to a pitch 338b of 0.75 mm at the distal end of the head. As a result of this graduated pitch, the bone screw 310 is a compression screw, since at least a portion of the helical thread 324 will be outside of the thread grooves formed in the bone by the passage of the shank threads 344. The head 312 may further include a cutting flute formed at the distal end of the helical thread 324, which acts to clear out bone material as the screw 310 is driven into bone, to ease the transition from the shank 314 to the head 312.

By way of example, the shank 314 is cylindrical in shape, and extends from a proximal end adjacent the neck 316 to the distal end 320 of the bone screw 310. The shank 314 comprises a curved lateral surface 342 and a helical thread 344 disposed around the curved lateral surface 342. The shank 314 may have a minor diameter within the range of 1.0 mm to 7.5 mm and a major diameter within the range of 1.5 mm to 8 mm. Preferably, the major diameter of the shank 314 is less than the major diameter of the head 312. In the example shown and described herein, the shank 314 has a minor diameter of 3 mm and a major diameter of approximately 4 mm. The helical thread 344 may have a pitch 346 within the range of 0.5 mm to 2.5 mm. By way of example, the helical thread 344 of the present example has a 1.5 mm pitch. The shank 314 further includes one or more cutting flutes 348 disposed at the distal end 320. The cutting flute 348 acts to clear out bone material as the screw 310 is driven into bone, which obviates the need for drilling a pilot hole during the surgical procedure.

The neck 316 comprises a curved lateral surface 350 that is tapered in the distal direction, to provide a smooth transition between the reverse conical head 312 and the shank 314.

The bone screw 310 further includes a central lumen extending axially through the entirety of the screw 310, identical to the central lumen shown and described above with respect to bone screw 310. The central lumen is sized and configured to receive a guide wire (e.g. K-wire) therethrough to guide the bone screw 310 to the correct implantation location.

Figure 16:
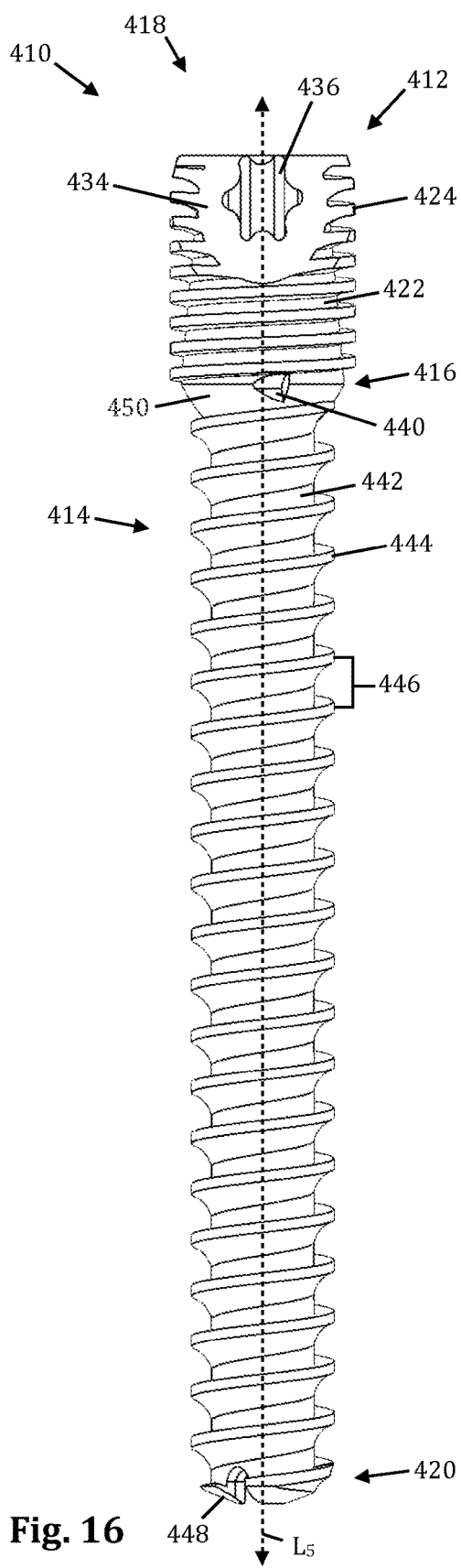
FIG. 16 is a front plan view of a fifth example of a bone screw according to an embodiment of the disclosure.
Figure 17:
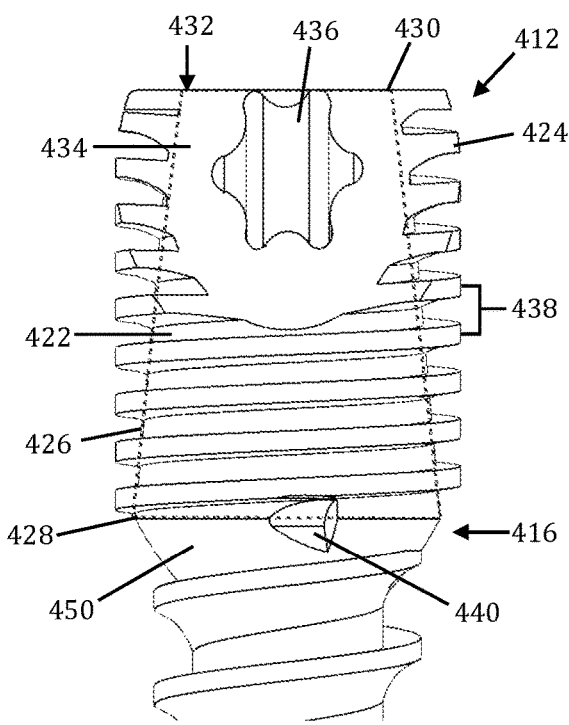
FIG. 17 is a front plan view of the head region of the bone screw of FIG. 16.
Figure 18:
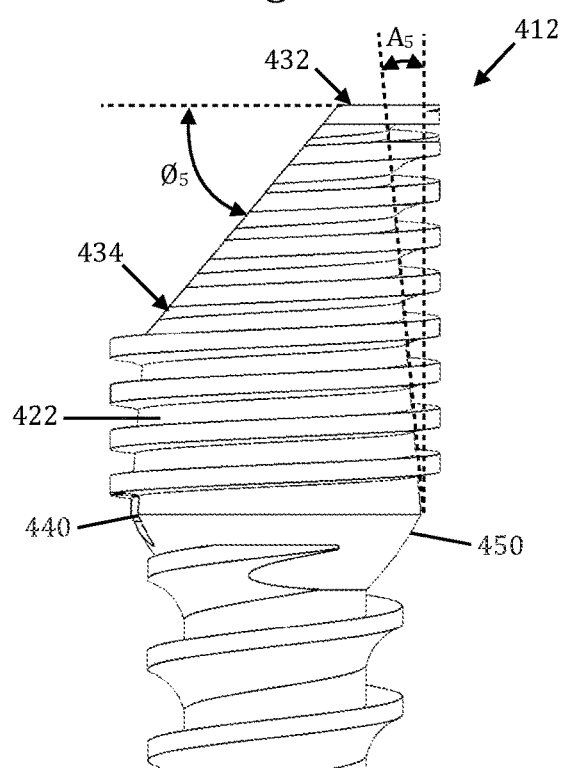
FIG. 18 is a side plan view of the head region of FIG. 17.

FIGS. 16-18 illustrate an example of a bone screw 410 according to another embodiment of the disclosure. By way of example, the bone screw 410 includes a head 412, a shank 414, and a neck 416 positioned between the head 412 and shank 414. The bone screw 410 further comprises a proximal end 418 and a distal end 420. The head 412 is positioned at/near the proximal end 418 of the bone screw 410, and the shank 414 extends axially along a longitudinal axis $L_5$ (also "vertical axis") from the neck 416 to the distal end 420 of the bone screw 410. The head 412 comprises a curved lateral surface 422 and a helical thread 424 disposed around the curved lateral surface 422. The head 412 has a reverse frustoconical cross-sectional shape 426 as described above with respect to bone screw 10. The curved lateral surface 422 is tapered in the proximal direction from the wide base 428 to the narrow base 430. By way of example, the curved lateral surface 422 is tapered at an angle $A_5$ of 5.9° relative to the longitudinal axis $L_5$ (resulting in the cone defining the shape of the head having an included angle of 11.8°), however the angle $A_5$ may be within the range of 4-15° (8-30° inclusive angle) without departing from the scope of the disclosure.

The head 412 may have a minor diameter within the range of 1.75 mm to 9.0 mm at the wide base 428. The head 412 has a major diameter within the range of 2.0 mm to 10.0 mm. The first minor diameter is less than the major diameter (of the helical thread 424). By way of example, the head 412 of the bone screw 410 shown in FIGS. 16-18 has a minor diameter of approximately 4.5 mm at the wide base 428 and a major diameter of approximately 5.0 mm. As a result of the frustoconical shape, the head 412 has a minor diameter that increases in a proximal to distal direction. The major diameter remains constant, and as a result the thread surface area in contact with bone increases in a distal to proximal direction, enhancing the purchase of the screw into the bone.

The head 412 further includes an angled surface 434 (also "chamfer" or "bevel") and a driver recess 436. The angled surface 434 is formed between the top surface 432 and the lateral surface 422. The top surface 432 has a width dimension that is greater than zero as measured along a diameter of the head, ensuring that the angled surface 434 does not extend completely across the top of the screw 410. In the instant example, the top surface 432 has a width dimension of 0.65 mm, however the width dimension may be more or less depending upon the overall size of the bone screw 410. By way of example, the angled surface 434 may have a bevel angle $Ø_5$ within the range of 1-60° measured from the plane of the top surface 432, which is generally perpendicular to the longitudinal axis $L_1$. By way of example the bevel angle $Ø_5$ of the bone screw 410 shown in FIGS. 16-18 is 50°. The angled surface 434 is positioned generally parallel to and flush with an exterior surface of the bone forming part of the anatomical target site when the head is implanted during use to thereby reduce or eliminate a degree to which the head will extend beyond the exterior surface of the bone when the bone screw 410 is implanted at an angle relative to the bone structure. The driver recess 436 is formed into the top surface 432 and angled surface 434 along the longitudinal axis $L_5$, and may have any shape suitable to receive a driver (e.g. flathead, Phillips-type, hexalobe, torx, etc.).

The helical thread 424 may have a pitch 438 within the range of 0.5 mm to 2.5 mm. By way of example, the helical thread 424 of the present example has a 0.75 mm pitch. The head 412 may further include a cutting flute 440 formed at the distal end of the helical thread 424, which acts to clear out bone material as the screw 410 is driven into bone, to ease the transition from the shank 414 to the head 412.

By way of example, the shank 414 is cylindrical in shape, and extends from a proximal end adjacent the neck 416 to the distal end 420 of the bone screw 410. The shank 414 comprises a curved lateral surface 442 and a helical thread 444 disposed around the curved lateral surface 442. The shank 414 may have a minor diameter within the range of 1.0 mm to 7.5 mm and a major diameter within the range of 1.5 mm to 8 mm. Preferably, the major diameter of the shank 414 is less than the major diameter of the head 412. In the example shown and described herein, the shank 414 has a minor diameter of 3 mm and a major diameter of approximately 4 mm. The helical thread 444 may have a pitch 446 within the range of 0.5 mm to 2.5 mm. By way of example, the helical thread 444 of the present example has a 1.5 mm pitch. Since the pitch 446 of the shank 414 is an even multiple (e.g. 2×) of the pitch 438 of the head 412, the bone screw 410 is compression-neutral. The shank 414 further includes one or more cutting flutes 448 disposed at the distal end 420. The cutting flute 448 acts to clear out bone material as the screw 410 is driven into bone, which obviates the need for drilling a pilot hole during the surgical procedure.

The neck 416 comprises a curved lateral surface 450 that is tapered in the distal direction, to provide a smooth transition between the reverse conical head 412 and the shank 414.

Figure 19:
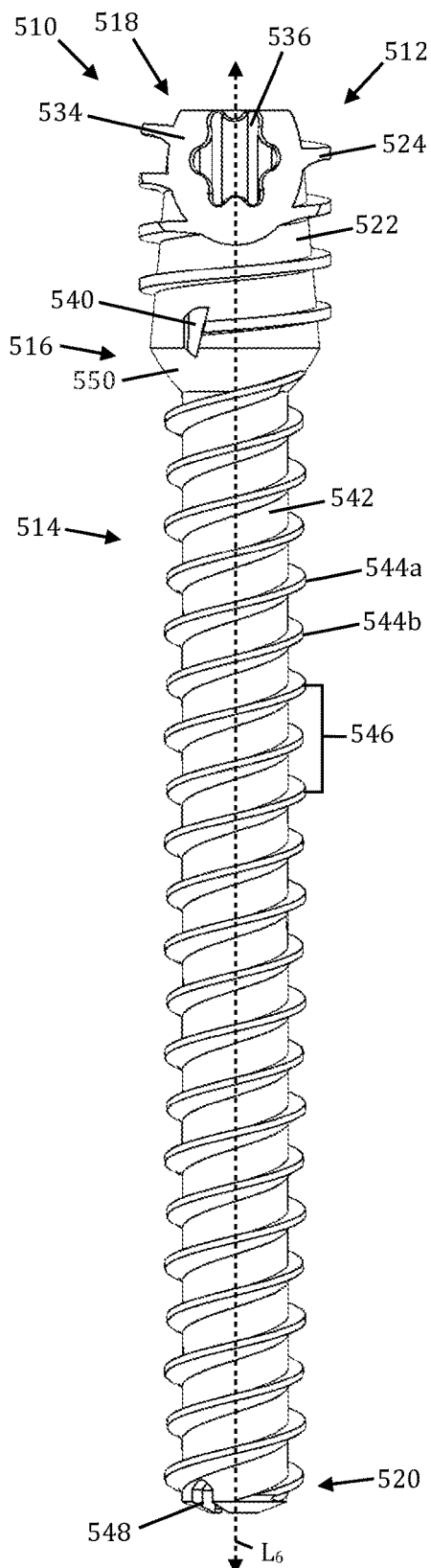
FIG. 19 is a front plan view of a sixth example of a bone screw according to an embodiment of the disclosure.
Figure 20:
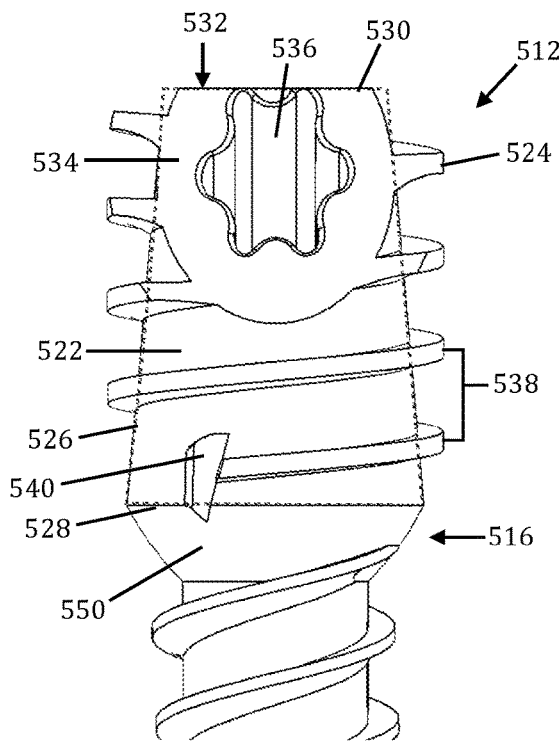
FIG. 20 is a front plan view of the head region of the bone screw of FIG. 19.
Figure 21:
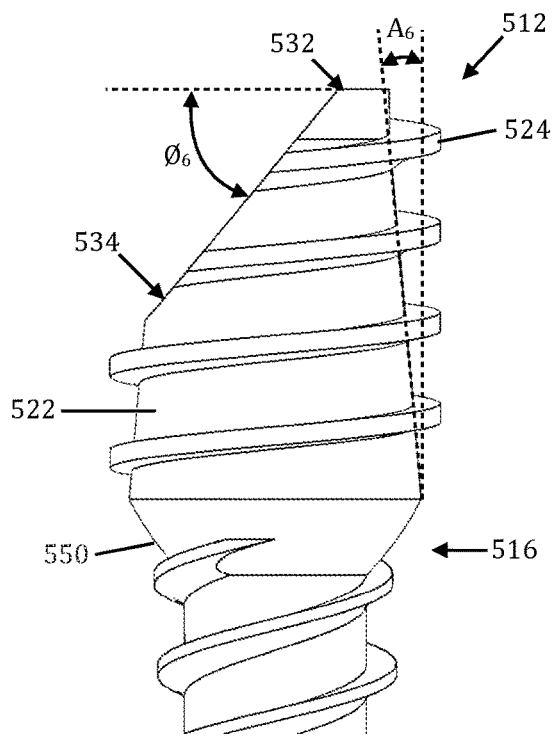
FIG. 21 is a side plan view of the head region of FIG. 20.

FIGS. 19-21 illustrate an example of a bone screw 510 according to another embodiment of the disclosure. By way of example, the bone screw 510 includes a head 512, a shank 514, and a neck 516 positioned between the head 512 and shank 514. The bone screw 510 further comprises a proximal end 518 and a distal end 520. The head 512 is positioned at/near the proximal end 518 of the bone screw 510, and the shank 514 extends axially along a longitudinal axis $L_6$ (also "vertical axis") from the neck 516 to the distal end 520 of the bone screw 510. The head 512 comprises a curved lateral surface 522 and a helical thread 524 disposed around the curved lateral surface 522. The head 512 has a reverse frustoconical cross-sectional shape 526 as described above with respect to bone screw 10. The curved lateral surface 522 is tapered in the proximal direction from the wide base 528 to the narrow base 530. By way of example, the curved lateral surface 522 is tapered at an angle $A_5$ of 5.9° relative to the longitudinal axis $L_5$ (resulting in the cone defining the shape of the head having an included angle of 11.8°), however the angle $A_5$ may be within the range of 4-15° (8-30° inclusive angle) without departing from the scope of the disclosure.

The head 512 may have a minor diameter within the range of 1.75 mm to 9.0 mm at the wide base 528. The head 512 has a major diameter within the range of 2.0 mm to 10.0 mm. The first minor diameter is less than the major diameter (of the helical thread 524). By way of example, the head 512 of the bone screw 510 shown in FIGS. 19-21 has a minor diameter of approximately 4.5 mm at the wide base 528 and a major diameter of approximately 5.0 mm. As a result of the frustoconical shape, the head 512 has a minor diameter that increases in a proximal to distal direction. The major diameter remains constant, and as a result the thread surface area in contact with bone increases in a distal to proximal direction, enhancing the purchase of the screw into the bone.

The head 512 further includes an angled surface 534 (also "chamfer" or "bevel") and a driver recess 536. The angled surface 534 is formed between the top surface 532 and the lateral surface 522. The top surface 532 has a width dimension that is greater than zero as measured along a diameter of the head, ensuring that the angled surface 534 does not extend completely across the top of the screw 510. In the instant example, the top surface 532 has a width dimension of 0.65 mm, however the width dimension may be more or less depending upon the overall size of the bone screw 510. By way of example, the angled surface 534 may have a bevel angle $Ø_6$ within the range of 1-60° measured from the plane of the top surface 532, which is generally perpendicular to the longitudinal axis $L_6$. By way of example, the bevel angle $Ø_6$ of the bone screw 510 shown in FIGS. 19-21 is 50°. The angled surface 534 is positioned generally parallel to and flush with an exterior surface of the bone forming part of the anatomical target site when the head is implanted during use to thereby reduce or eliminate a degree to which the head will extend beyond the exterior surface of the bone when the bone screw 510 is implanted at an angle relative to the bone structure. The driver recess 536 is formed into the top surface 532 and angled surface 534 along the longitudinal axis $L_6$, and may have any shape suitable to receive a driver (e.g. flathead, Phillips-type, hexalobe, torx, etc.).

The helical thread 524 may have a pitch 538 within the range of 0.5 mm to 2.5 mm. By way of example, the helical thread 524 of the present example has a 1.5 mm pitch. The head 512 may further include a cutting flute 540 formed at the distal end of the helical thread 524, which acts to clear out bone material as the screw 510 is driven into bone, to ease the transition from the shank 514 to the head 512.

By way of example, the shank 514 is cylindrical in shape, and extends from a proximal end adjacent the neck 516 to the distal end 520 of the bone screw 510. The shank 514 comprises a curved lateral surface 542 and a pair of helical threads 544a, 544b disposed around the curved lateral surface 542. The shank 514 may have a minor diameter within the range of 1.0 mm to 7.5 mm and a major diameter within the range of 1.5 mm to 8 mm. Preferably, the major diameter of the shank 514 is less than the major diameter of the head 512. In the example shown and described herein, the shank 514 has a minor diameter of 3 mm and a major diameter of approximately 4 mm. The helical threads 544a, 544b may have a pitch 546 within the range of 0.5 mm to 5.0 mm. By way of example, the helical threads 544a, 544b of the present example each have a 3.0 mm pitch (e.g. distance between adjacent threads of the same helix), however there are two helical threads 544a, 544b that are spaced evenly apart, making the effective pitch of the bone screw 510 1.5 mm which is the same as the pitch of the helical thread 524 of the head 512. Because the bone screw 510 uses a double helix configuration in the shank thread, the bone screw 510 is capable of being driven into the target bone at a rate approximately twice as fast as with a bone screw having a true pitch of 1.5 mm. Because the head 512 and shank 514 have the same pitch (or effective pitch), the bone screw 510 is compression neutral. The shank 514 further includes one or more cutting flutes 548 disposed at the distal end 520. The cutting flute 548 acts to clear out bone material as the screw 510 is driven into bone, which obviates the need for drilling a pilot hole during the surgical procedure.

The neck 516 comprises a curved lateral surface 550 that is tapered in the distal direction, to provide a smooth transition between the reverse conical head 512 and the shank 514.

The bone screw 510 further includes a central lumen extending axially through the entirety of the screw 510 similar to the central lumen 52 shown and described above with respect to the bone screw 10. The central lumen 552 is sized and configured to receive a guide wire (e.g. K-wire) therethrough to guide the bone screw 510 to the correct implantation location.

FIGS. 22-24 illustrate an example of a bone screw 610 according to another embodiment of the disclosure. By way of example, the bone screw 610 includes a head 612, a shank 614, and a neck 616 positioned between the head 612 and shank 614. The bone screw 610 further comprises a proximal end 618 and a distal end 620. The head 612 is positioned at/near the proximal end 618 of the bone screw 610, and the shank 614 extends axially along a longitudinal axis $L_7$ (also "vertical axis") from the neck 616 to the distal end 620 of the bone screw 610. The head 612 comprises a curved lateral surface 622 and a helical thread 624 disposed around the curved lateral surface 622. The head 612 has a reverse frustoconical cross-sectional shape 626 as described above with respect to bone screw 10. The curved lateral surface 622 is tapered in the proximal direction from the wide base 628 to the narrow base 630. By way of example, the curved lateral surface 622 is tapered at an angle $A_7$ of 5.9° relative to the longitudinal axis $L_7$ (resulting in the cone defining the shape of the head having an included angle of 11.8°), however the angle $A_7$ may be within the range of 4-15° (8-30° inclusive angle) without departing from the scope of the disclosure.

The head 612 may have a minor diameter within the range of 1.75 mm to 9.0 mm at the wide base 628 and a major diameter within the range of 2.0 mm to 10.0 mm. The first minor diameter is less than the major diameter (of the helical thread 624). By way of example, the head 612 of the bone screw 610 shown in FIGS. 22-24 has a minor diameter of approximately 4.5 mm at the wide base 628 and a major diameter of approximately 5.0 mm. As a result of the frustoconical shape, the head 612 has a minor diameter that increases in a proximal to distal direction. The thread 624 has a proximally-oriented outward taper 625 having a taper angle $B_7$ of approximately 10° (for example, with a range of 5-30°) so that the major diameter at the proximal end 618 is greater than the major diameter near the neck 616, and as a result (and in combination with the reverse frustoconical shape of the head 612), the surface area of the helical thread 624 in contact with bone increases in a distal to proximal direction, enhancing the purchase of the screw into the bone. In this example embodiment, the combination of the reverse frustoconical shape of the head 612 and the outward taper 625 of the thread 624 (e.g. angles $A_7+B_7$) maximizes the surface area of the threads 624 that is in contact with bone.

The head 612 further includes an angled surface 634 (also "chamfer" or "bevel") and a driver recess 636. The angled surface 634 is formed between the top surface 632 and the lateral surface 622. The top surface 632 has a width dimension that is greater than zero as measured along a diameter of the head, ensuring that the angled surface 634 does not extend completely across the top of the screw 610. In the instant example, the top surface 632 has a width dimension of 0.65 mm, however the width dimension may be more or less depending upon the overall size of the bone screw 610. By way of example, the angled surface 634 may have a bevel angle $Ø_7$ within the range of 1-60° measured from the plane of the top surface 632, which is generally perpendicular to the longitudinal axis $L_7$. By way of example, the bevel angle $Ø_7$ of the bone screw 610 shown in FIGS. 22-24 is 50°. The angled surface 634 is positioned generally parallel to and flush with an exterior surface of the bone forming part of the anatomical target site when the head is implanted during use to thereby reduce or eliminate a degree to which the head will extend beyond the exterior surface of the bone when the bone screw 610 is implanted at an angle relative to the bone structure. The driver recess 636 is formed into the top surface 632 and angled surface 634 along the longitudinal axis $L_7$, and may have any shape suitable to receive a driver (e.g. flathead, Phillips-type, hexalobe, torx, etc.). The helical thread 624 may have a pitch 638 within the range of 0.5 mm to 2.5 mm. By way of example, the helical thread 624 of the present example has a 0.75 mm pitch.

By way of example, the shank 614 is cylindrical in shape, and extends from a proximal end adjacent the neck 616 to the distal end 620 of the bone screw 610. The shank 614 comprises a curved lateral surface 642 and a helical thread 644 disposed around the curved lateral surface 642. The shank 614 may have a minor diameter within the range of 1.0 mm to 7.5 mm and a major diameter within the range of 1.5 mm to 8 mm. Preferably, the major diameter of the shank 614 is less than the major diameter of the head 612. In the example shown and described herein, the shank 614 has a minor diameter of 3 mm and a major diameter of approximately 4 mm. The helical thread 644 may have a pitch 646 within the range of 0.5 mm to 2.5 mm. By way of example, the helical thread 644 of the present example has a 1.5 mm pitch, which is the same as the pitch of the helical thread 624 of the head 612. Because the head 612 and shank 614 have the same pitch, the bone screw 610 is compression neutral. The shank 614 further includes one or more cutting flutes 648 disposed at the distal end 620. The cutting flute 648 acts to clear out bone material as the screw 610 is driven into bone, which obviates the need for drilling a pilot hole during the surgical procedure.

The neck 616 comprises a curved lateral surface 650 that is tapered in the distal direction, to provide a smooth transition between the reverse conical head 612 and the shank 614.

The bone screw 610 further includes a central lumen extending axially through the entirety of the screw 610, identical to the central lumen 52 shown and described above with respect to bone screw 10. The central lumen is sized and configured to receive a guide wire (e.g. K-wire) therethrough to guide the bone screw 610 to the correct implantation location.

Figure 25:
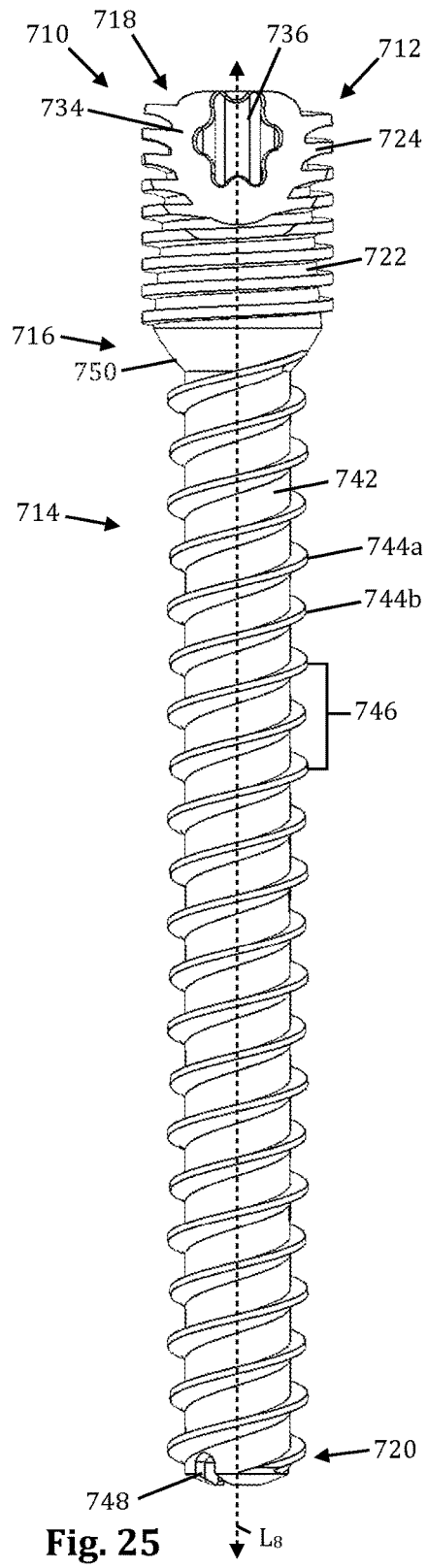
FIG. 25 is a front plan view of a eighth example of a bone screw according to an embodiment of the disclosure.
Figure 26:
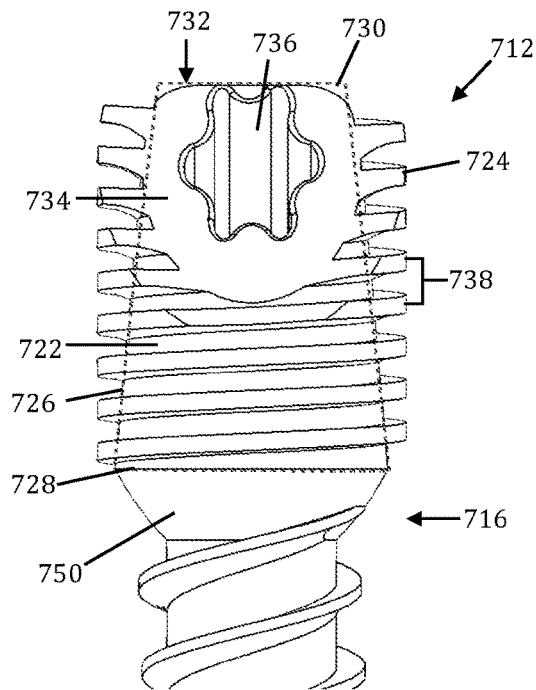
FIG. 26 is a front plan view of the head region of the bone screw of FIG. 25.
Figure 27:
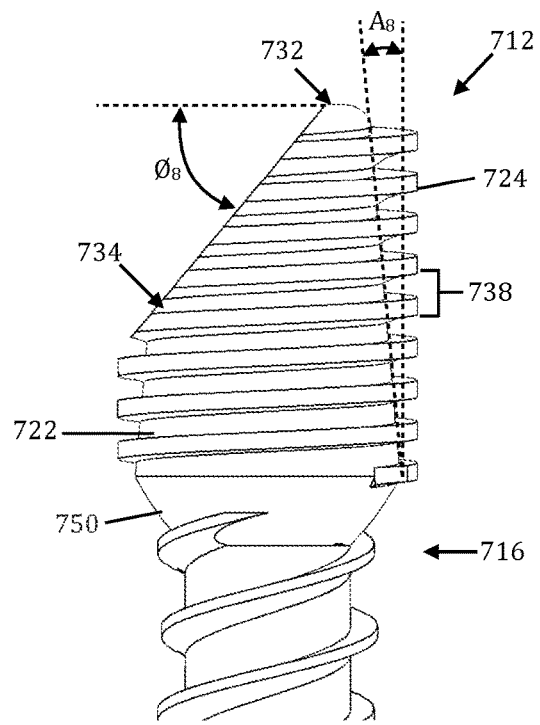
FIG. 27 is a side plan view of the head region of FIG. 26.

FIGS. 25-27 illustrate an example of a bone screw 710 according to another embodiment of the disclosure. By way of example, the bone screw 710 includes a head 712, a shank 714, and a neck 716 positioned between the head 712 and shank 714. The bone screw 710 further comprises a proximal end 718 and a distal end 720. The head 712 is positioned at/near the proximal end 718 of the bone screw 710, and the shank 714 extends axially along a longitudinal axis $L_8$ (also "vertical axis") from the neck 716 to the distal end 720 of the bone screw 710. The head 712 comprises a curved lateral surface 722 and a helical thread 724 disposed around the curved lateral surface 722. The head 712 has a reverse frustoconical cross-sectional shape 726 as described above with respect to bone screw 10. The curved lateral surface 22 is tapered in the proximal direction from the wide base 28 to the narrow base 30. By way of example, the curved lateral surface 22 is tapered at an angle $A_1$ of 5.9° relative to the longitudinal axis $L_1$ (resulting in the cone defining the shape of the head having an included angle of 11.8°), however the angle $A_1$ may be within the range of 4-15° (8-30° inclusive angle) without departing from the scope of the disclosure.

The head 712 may have a minor diameter within the range of 1.75 mm to 9.0 mm at the wide base 728 and a major diameter within the range of 2.0 mm to 10.0 mm. The first minor diameter is less than the major diameter (of the helical thread 724). By way of example, the head 712 of the bone screw 710 shown in FIGS. 25-27 has a minor diameter of approximately 4.5 mm at the wide base 728 and a major diameter of approximately 5.0 mm. As a result of the frustoconical shape, the head 712 has a minor diameter that increases in a proximal to distal direction. The thread 724 has a 10° (for example) proximally-oriented outward taper 725 so that the major diameter at the proximal end 718 is greater than the major diameter near the neck 716, and as a result (and in combination with the reverse frustoconical shape of the head 712), the surface area of the helical thread 724 in contact with bone increases in a distal to proximal direction, enhancing the purchase of the screw into the bone.

The head 712 further includes an angled surface 734 (also "chamfer" or "bevel") and a driver recess 736. The angled surface 734 is formed between the top surface 732 and the lateral surface 722. The top surface 732 has a width dimension that is greater than zero as measured along a diameter of the head, ensuring that the angled surface 734 does not extend completely across the top of the screw 710. In the instant example, the top surface 732 has a width dimension of 0.65 mm, however the width dimension may be more or less depending upon the overall size of the bone screw 710. By way of example, the angled surface 734 may have a bevel angle $Ø_8$ within the range of 1-60° measured from the plane of the top surface 732, which is generally perpendicular to the longitudinal axis $L_8$. By way of example, the bevel angle $Ø_8$ of the bone screw 710 shown in FIGS. 25-27 is 50°. The angled surface 734 is positioned generally parallel to and flush with an exterior surface of the bone forming part of the anatomical target site when the head is implanted during use to thereby reduce or eliminate a degree to which the head will extend beyond the exterior surface of the bone when the bone screw 710 is implanted at an angle relative to the bone structure. The driver recess 736 is formed into the top surface 732 and the angled surface 734 along the longitudinal axis $L_8$, and may have any shape suitable to receive a driver (e.g. flathead, Phillips-type, hexalobe, torx, etc.). The helical thread 724 may have a pitch 738 within the range of 0.5 mm to 2.5 mm. By way of example, the helical thread 724 of the present example has a 0.75 mm pitch.

By way of example, the shank 714 is cylindrical in shape, and extends from a proximal end adjacent the neck 716 to the distal end 720 of the bone screw 710. The shank 714 comprises a curved lateral surface 742 and a pair of helical threads 744a, 744b disposed around the curved lateral surface 742. The shank 714 may have a minor diameter within the range of 1.0 mm to 7.5 mm and a major diameter within the range of 1.5 mm to 8 mm. Preferably, the major diameter of the shank 714 is less than the major diameter of the head 712. In the example shown and described herein, the shank 714 has a minor diameter of 3 mm and a major diameter of approximately 4 mm. The helical threads 744a, 744b may have a pitch 746 within the range of 0.5 mm to 2.5 mm. By way of example, the helical threads 744a, 744b of the present example each have a 3.0 mm pitch (e.g. distance between adjacent threads of the same helix), however there are two helical threads 744a, 744b that are spaced evenly apart, making the effective pitch of the bone screw 710 1.5 mm which is the same as the pitch of the helical thread 724 of the head 712. Because the bone screw 710 uses a double helix configuration in the shank thread, the bone screw 710 is capable of being driven into the target bone at a rate approximately twice as fast as with a bone screw having a true pitch of 1.5 mm. Since the pitch 746 of the shank 714 is an even multiple (e.g. 2×) of the pitch 738 of the head 712, the bone screw 710 is compression-neutral. The shank 714 further includes one or more cutting flutes 748 disposed at the distal end 720. The cutting flute 748 acts to clear out bone material as the screw 710 is driven into bone, which obviates the need for drilling a pilot hole during the surgical procedure.

The neck 716 comprises a curved lateral surface 750 that is tapered in the distal direction, to provide a smooth transition between the reverse conical head 712 and the shank 714.

The bone screw 710 further includes a central lumen extending axially through the entirety of the screw 710 similar to the central lumen 52 shown and described above with respect to the bone screw 10. The central lumen is sized and configured to receive a guide wire (e.g. K-wire) therethrough to guide the bone screw 710 to the correct implantation location.

FIGS. 28-30 illustrate an example of a bone screw 810 according to another embodiment of the disclosure. By way of example, the bone screw 810 described herein may be useful in situations in which the bone screw 810 is not implanted at an extreme angle. The bone screw 810 includes a head 812, a shank 814, and a neck 816 positioned between the head 812 and shank 814. The bone screw 810 further comprises a proximal end 818 and a distal end 820. The head 812 is positioned at/near the proximal end 818 of the bone screw 810, and the shank 814 extends axially along a longitudinal axis $L_9$ (also "vertical axis") from the neck 816 to the distal end 820 of the bone screw 810. The head 812 comprises a curved lateral surface 822 and a helical thread 824 disposed around the curved lateral surface 822. The head 812 has a reverse frustoconical cross-sectional shape 826 as described above with respect to bone screw 10. The curved lateral surface 822 is tapered in the proximal direction from the wide base 828 to the narrow base 830. By way of example, the curved lateral surface 822 is tapered at an angle $A_9$ of 5.9° relative to the longitudinal axis $L_9$ (resulting in the cone defining the shape of the head having an included angle of 11.8°), however the angle $A_9$ may be within the range of 4-15° (8-30° inclusive angle) without departing from the scope of the disclosure.

The head 812 may have a minor diameter within the range of 1.75 mm to 9.0 mm at the wide base 828 and a major diameter within the range of 2.0 mm to 10.0 mm. The first minor diameter is less than the major diameter (of the helical thread 824). By way of example, the head 812 of the bone screw 810 shown in FIGS. 28-30 has a minor diameter of approximately 4.5 mm at the wide base 828 and a major diameter of approximately 5.0 mm. As a result of the frustoconical shape, the head 812 has a minor diameter that increases in a proximal to distal direction. The major diameter remains constant, and as a result the thread surface area in contact with bone increases in a distal to proximal direction, enhancing the purchase of the screw into the bone. The head 812 further includes a driver recess 836 formed into the top surface 832 along the longitudinal axis $L_9$, and may have any shape suitable to receive a driver (e.g. flathead, Phillips-type, hexalobe, torx, etc.). The helical thread 824 may have a pitch 838 (e.g. the distance between adjacent threads at any one location) within the range of 0.5 mm to 2.5 mm. By way of example, the helical thread 824 of the present example has a 1.5 mm pitch.

The bone screw 810 of the instant embodiment is one example of a bone screw in which the "bevel angle" is 0°. This results in a flat head 812, wherein the top surface 832 and angled surface 834 are essentially the same surface.

By way of example, the shank 814 is cylindrical in shape, and extends from a proximal end adjacent the neck 816 to the distal end 820 of the bone screw 810. The shank 814 comprises a curved lateral surface 842 and a helical thread 844 disposed around the curved lateral surface 842. The shank 814 may have a minor diameter within the range of 1.0 mm to 7.5 mm and a major diameter within the range of 1.5 mm to 8 mm. Preferably, the major diameter of the shank 814 is less than the major diameter of the head 812. In the example shown and described herein, the shank 814 has a minor diameter of 3 mm and a major diameter of approximately 4 mm. The helical thread 844 may have a pitch 846 within the range of 0.5 mm to 2.5 mm. By way of example, the helical thread 844 of the present example has a 1.5 mm pitch, which is the same as the pitch of the helical thread 824 of the head 812. Because the head 812 and shank 814 have the same pitch, the bone screw 810 is compression neutral. The shank 814 further includes one or more cutting flutes 848 disposed at the distal end 820. The cutting flute(s) 848 acts to clear out bone material as the screw 810 is driven into bone, which obviates the need for drilling a pilot hole during the surgical procedure.

The neck 816 comprises a curved lateral surface 850 that is tapered in the distal direction, to provide a smooth transition between the reverse conical head 812 and the shank 814.

The bone screw 810 further includes a central lumen extending axially through the entirety of the screw 810. The central lumen is sized and configured to receive a guide wire (e.g. K-wire) therethrough to guide the bone screw 810 to the correct implantation location.

Figure 32:
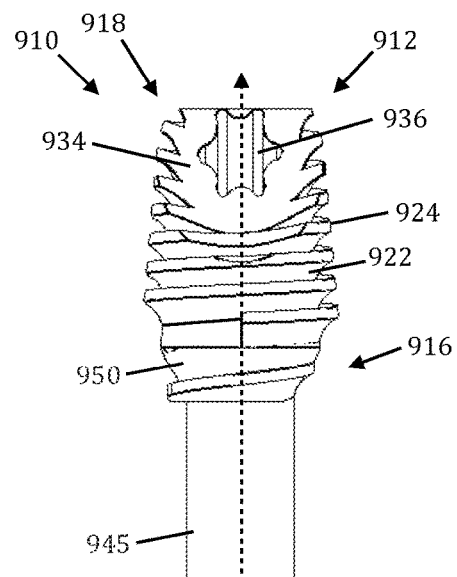
FIG. 32 is a front plan view of the head region of the bone screw of FIG. 28.
Figure 32:
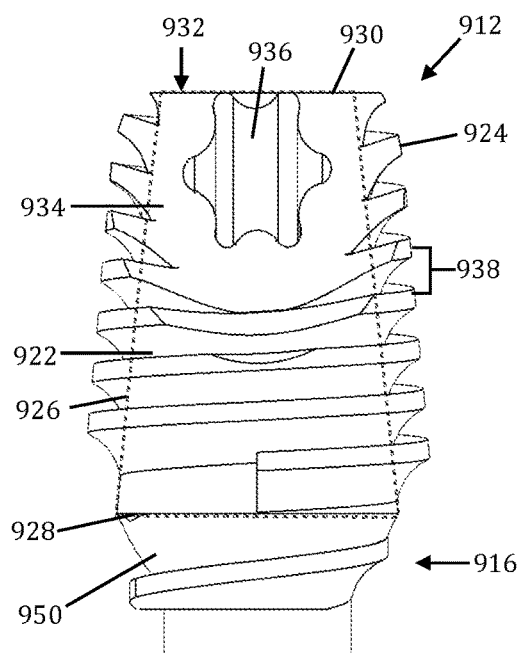
Figure 31:
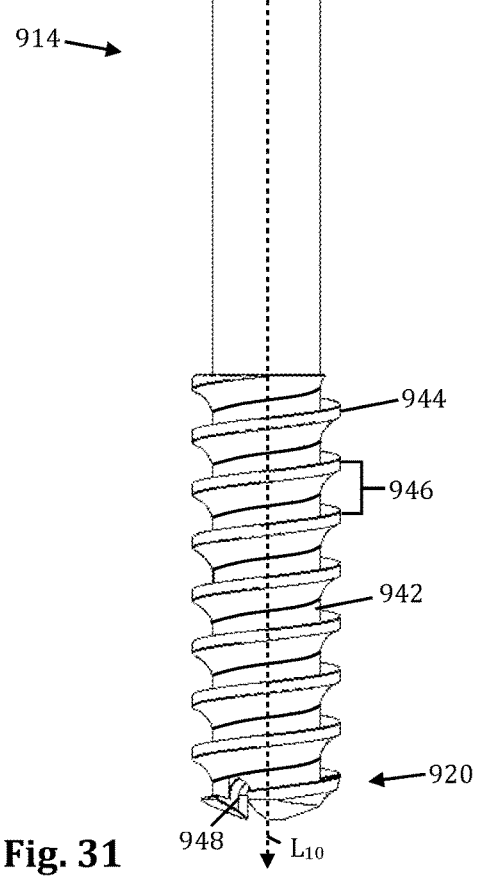
FIG. 31 is a front plan view of a tenth example of a bone screw according to an embodiment of the disclosure.
Figure 33:
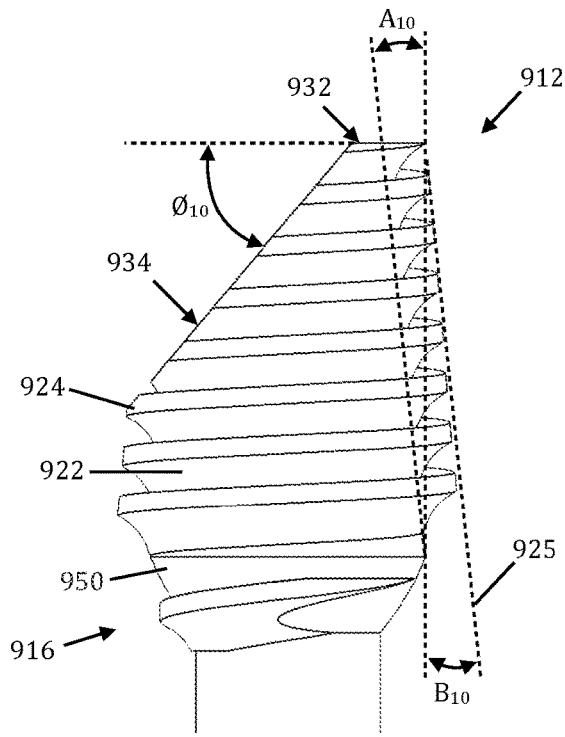
FIG. 33 is a side plan view of the head region of FIG. 31.

FIGS. 31-33 illustrate an example of a bone screw 910 according to another embodiment of the disclosure. By way of example, the bone screw 910 includes a head 912, a shank 914, and a neck 916 positioned between the head 912 and shank 914. The bone screw 910 further comprises a proximal end 918 and a distal end 920. The head 912 is positioned at/near the proximal end 918 of the bone screw 910, and the shank 914 extends axially along a longitudinal axis $L_{10}$ (also "vertical axis") from the neck 916 to the distal end 920 of the bone screw 910. The head 912 comprises a curved lateral surface 922 and a helical thread 924 disposed around the curved lateral surface 922. The head 912 has a reverse frustoconical cross-sectional shape 926 as described above with respect to bone screw 10. The curved lateral surface 922 is tapered in the proximal direction from the wide base 928 to the narrow base 930. By way of example, the curved lateral surface 922 is tapered at an angle $A_{10}$ of 5.9° relative to the longitudinal axis $L_{10}$ (resulting in the cone defining the shape of the head having an included angle of 11.8°), however the angle $A_{10}$ may be within the range of 4-15° (8-30° inclusive angle) without departing from the scope of the disclosure.

The head 912 may have a minor diameter within the range of 1.75 mm to 9.0 mm at the wide base 928 and a major diameter within the range of 2.0 mm to 10.0 mm. The first minor diameter is less than the major diameter (of the helical thread 924). By way of example, the head 912 of the bone screw 910 shown in FIGS. 31-33 has a minor diameter of approximately 4.5 mm at the wide base 428 and a major diameter of approximately 5.0 mm. As a result of the frustoconical shape, the head 912 has a minor diameter that increases in a proximal to distal direction. The thread 924 has a proximally-oriented inward taper 925 so that the major diameter at the proximal end 918 is less than the major diameter near the neck 916. By way of example, the inward taper 925 of the thread 924 is parallel to the taper of the curved lateral surface 922. As such, the thread 924 is tapered at an angle $B_{10}$ of 5.9° relative to the longitudinal axis $L_{10}$, however the angle $B_{10}$ may be within the range of 5-15° without departing from the scope of the disclosure.

The head 912 further includes an angled surface 934 (also "chamfer" or "bevel") and a driver recess 936. The angled surface 934 is formed between the top surface 932 and the lateral surface 922. The top surface 932 has a width dimension that is greater than zero as measured along a diameter of the head, ensuring that the angled surface 934 does not extend completely across the top of the screw 910. In the instant example, the top surface 932 has a width dimension of 0.65 mm, however the width dimension may be more or less depending upon the overall size of the bone screw 910. By way of example, the angled surface 934 may have a bevel angle $Ø_{10}$ within the range of 1-60° measured from the plane of the top surface 932, which is generally perpendicular to the longitudinal axis $L_{10}$. By way of example, the bevel angle $Ø_{10}$ of the bone screw 910 shown in FIGS. 31-33 is 50°. The angled surface 934 is positioned generally parallel to and flush with an exterior surface of the bone forming part of the anatomical target site when the head is implanted during use to thereby reduce or eliminate a degree to which the head will extend beyond the exterior surface of the bone when the bone screw 910 is implanted at an angle relative to the bone structure. The driver recess 936 is formed into the top surface 932 and angled surface 934 along the longitudinal axis $L_{10}$, and may have any shape suitable to receive a driver (e.g. flathead, Phillips-type, hexalobe, torx, etc.).

The helical thread 924 may have a pitch 938 within the range of 0.5 mm to 2.5 mm. By way of example, the helical thread 924 of the present example has a 0.8 mm pitch. The head 912 may further include a cutting flute 940 formed at the distal end of the helical thread 924, which acts to clear out bone material as the screw 910 is driven into bone, to ease the transition from the shank 914 to the head 912.

By way of example, the shank 914 is cylindrical in shape, and extends from a proximal end adjacent the neck 916 to the distal end 920 of the bone screw 910. The shank 914 comprises a curved lateral surface 942 and a helical thread 944 disposed around a distal portion of the curved lateral surface 942. The shank further includes a proximally-positioned threadless section 945 to enable compression. By way of example, the threadless section 945 may comprise approximately two-thirds of the length of the shaft with the distal one-third length being threaded. Other configurations are possible depending on the type and location of the fracture being treated. The shank 914 may have a minor diameter within the range of 1.0 mm to 7.5 mm and a major diameter within the range of 1.5 mm to 8 mm. Preferably, the major diameter of the shank 914 is less than the major diameter of the head 912. In the example shown and described herein, the shank 914 has a minor diameter of 3 mm and a major diameter of approximately 4 mm. The helical thread 944 may have a pitch 946 within the range of 0.5 mm to 2.5 mm. By way of example, the helical thread 944 of the present example has a 1.5 mm pitch. Since the pitch 946 of the shank 914 is not an even multiple (e.g. 2×) of the pitch 938 of the head 912, the bone screw 910 is a compression screw. The shank 914 further includes one or more cutting flutes 948 disposed at the distal end 920. The cutting flute 948 acts to clear out bone material as the screw 910 is driven into bone, which obviates the need for drilling a pilot hole during the surgical procedure.

The neck 916 comprises a curved lateral surface 950 that is tapered in the distal direction, to provide a smooth transition between the reverse conical head 912 and the shank 914.

The bone screw 910 further includes a central lumen extending axially through the entirety of the screw 910. The central lumen is sized and configured to receive a guide wire (e.g. K-wire) therethrough to guide the bone screw 910 to the correct implantation location.

FIGS. 34-36 illustrate an example of a bone screw 1010 according to another embodiment of the disclosure. By way of example, the bone screw 1010 includes a head 1012, a shank 1014, and a neck 1016 positioned between the head 1012 and shank 1014. The bone screw 1010 further comprises a proximal end 1018 and a distal end 1020. The head 1012 is positioned at/near the proximal end 1018 of the bone screw 1010, and the shank 1014 extends axially along a longitudinal axis $L_{11}$ (also "vertical axis") from the neck 1016 to the distal end 1020 of the bone screw 1010. The head 1012 comprises a curved lateral surface 1022 and a helical thread 1024 disposed around the curved lateral surface 1022. The head 1012 has a reverse frustoconical cross-sectional shape 1026 as described above with respect to bone screw 10. The curved lateral surface 1022 is tapered in the proximal direction from the wide base 1028 to the narrow base 1030. By way of example, the curved lateral surface 1022 is tapered at an angle $A_{11}$ of 4.5° relative to the longitudinal axis $L_{11}$ (resulting in the cone defining the shape of the head having an included angle of 9°), however the angle $A_{11}$ may be within the range of 4-15° (8-30° inclusive angle) without departing from the scope of the disclosure.

The head 1012 may have a minor diameter within the range of 1.75 mm to 9.0 mm at the wide base 1028. The head 1012 has a major diameter within the range of 2.0 mm to 10.0 mm. The first minor diameter is less than the major diameter (of the helical thread 1024). By way of example, the head 1012 of the bone screw 1010 shown in FIGS. 34-36 has a minor diameter of approximately 3.4 mm at the wide base 1028 and a major diameter of approximately 4.0 mm. As a result of the frustoconical shape, the head 1012 has a minor diameter that increases in a proximal to distal direction. The major diameter remains constant, and as a result the thread surface area in contact with bone increases in a distal to proximal direction, enhancing the purchase of the screw into the bone.

The head 1012 further includes an angled surface 1034 (also "chamfer" or "bevel") and a driver recess 1036. The angled surface 1034 is formed between the top surface 1032 and the lateral surface 1022. The top surface 1032 has a width dimension that is greater than zero as measured along a diameter of the head, ensuring that the angled surface 1034 does not extend completely across the top of the screw 1010. In the instant example, the top surface 1032 has a width dimension of 0.45 mm, however the width dimension may be more or less depending upon the overall size of the bone screw 1010. By way of example, the angled surface 1034 may have a bevel angle $Ø_{ii}$ within the range of 1-60° measured from the plane of the top surface 1032, which is generally perpendicular to the longitudinal axis $L_{11}$. By way of example, the bevel angle $Ø_{ii}$ of the bone screw 1010 shown in FIGS. 34-36 is 50°. The angled surface 1034 is positioned generally parallel to and flush with an exterior surface of the bone forming part of the anatomical target site when the head is implanted during use to thereby reduce or eliminate a degree to which the head will extend beyond the exterior surface of the bone when the bone screw 1010 is implanted at an angle relative to the bone structure. The driver recess 1036 is formed into the top surface 1032 along the longitudinal axis $L_{11}$, and may have any shape suitable to receive a driver (e.g. flathead, Phillips-type, hexalobe, torx, etc.). By way of example, the helical thread 1024 of the present example has a 1.2 mm pitch.

By way of example, the shank 1014 is cylindrical in shape, and extends from a proximal end adjacent the neck 1016 to the distal end 1020 of the bone screw 1010. The shank 1014 comprises a curved lateral surface 1042 and a helical thread 1044 disposed around the curved lateral surface 1042. The shank 1014 may have a minor diameter within the range of 1.0 mm to 7.5 mm and a major diameter within the range of 1.5 mm to 8 mm. Preferably, the major diameter of the shank 1014 is less than the major diameter of the head 1012. In the example shown and described herein, the shank 1014 has a minor diameter of approximately 1.5 mm and a major diameter of approximately 2.5 mm. The helical thread 1044 may have a pitch 1046 within the range of 0.5 mm to 2.5 mm. By way of example, the helical thread 1044 of the present example has a 1.2 mm pitch, which is the same as the pitch of the helical thread 1024 of the head 1012. Because the head 1012 and shank 1014 have the same pitch, the bone screw 1010 is compression neutral. The shank 1014 further includes one or more cutting flutes 1048 disposed at the distal end 1020. The cutting flute 1048 acts to clear out bone material as the screw 1010 is driven into bone, which obviates the need for drilling a pilot hole during the surgical procedure.

The neck 1016 comprises a curved lateral surface 1050 that is tapered in the distal direction, to provide a smooth transition between the reverse conical head 1012 and the shank 1014.

The bone screw 1010 further includes a central lumen extending axially through the entirety of the screw 1010, identical to the central lumen shown and described above with respect to bone screw 1010. The central lumen is sized and configured to receive a guide wire (e.g. K-wire) therethrough to guide the bone screw 1010 to the correct implantation location.

Figure 37:
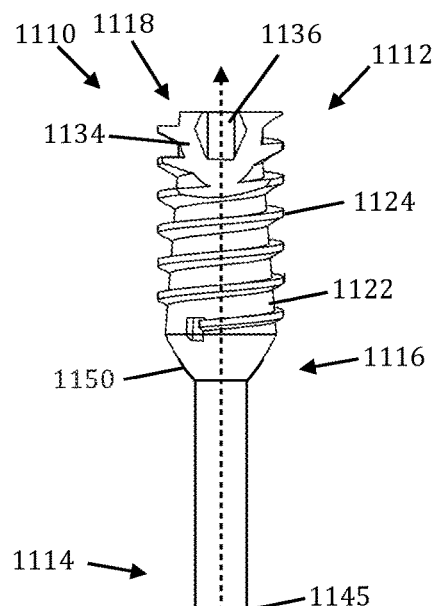
FIG. 37 is a front plan view of a twelfth example of a bone screw according to an embodiment of the disclosure.
Figure 38:
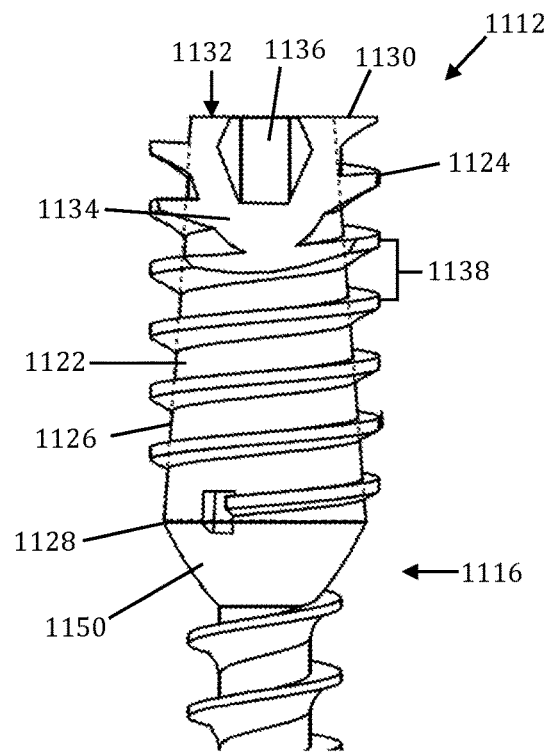
FIG. 38 is a front plan view of the head region of the bone screw of FIG. 37.
Figure 39:
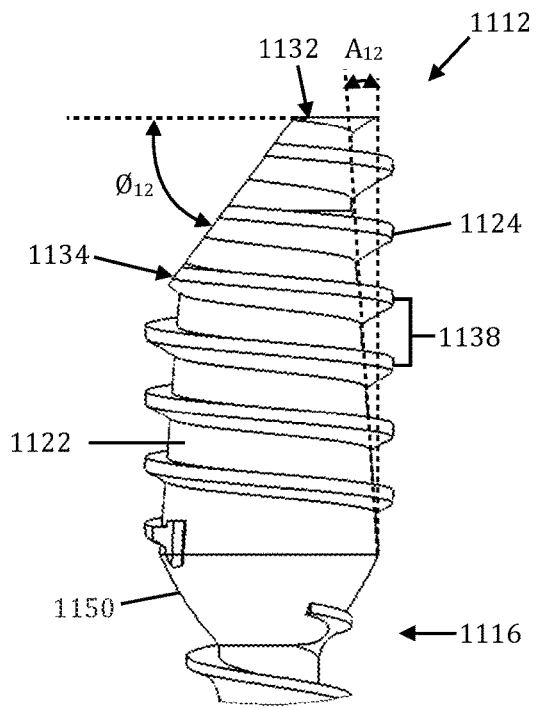
FIG. 39 is a side plan view of the head region of FIG. 37.

FIGS. 37-39 illustrate an example of a bone screw 1110 according to another embodiment of the disclosure. By way of example, the bone screw 1110 includes a head 1112, a shank 1114, and a neck 1116 positioned between the head 1112 and shank 1114. The bone screw 1110 further comprises a proximal end 1118 and a distal end 1120. The head 1112 is positioned at/near the proximal end 1118 of the bone screw 1110, and the shank 1114 extends axially along a longitudinal axis $L_{12}$ (also "vertical axis") from the neck 1116 to the distal end 1120 of the bone screw 1110. The head 1112 comprises a curved lateral surface 1122 and a helical thread 1124 disposed around the curved lateral surface 1122. The head 1112 has a reverse frustoconical cross-sectional shape 1126 as described above with respect to bone screw 10. The curved lateral surface 1122 is tapered in the proximal direction from the wide base 1128 to the narrow base 1130. By way of example, the curved lateral surface 1122 is tapered at an angle $A_{12}$ of 4.4° relative to the longitudinal axis $L_{12}$ (resulting in the cone defining the shape of the head having an included angle of 8.8°), however the angle $A_{12}$ may be within the range of 4-15° (8-30° inclusive angle) without departing from the scope of the disclosure.

The head 1112 may have a minor diameter within the range of 1.75 mm to 9.0 mm at the wide base 1128. The head 1112 has a major diameter within the range of 2.0 mm to 10.0 mm. The first minor diameter is less than the major diameter (of the helical thread 1124). By way of example, the head 1112 of the bone screw 1110 shown in FIGS. 37-39 has a minor diameter of approximately 3.3 mm at the wide base 1128 and a major diameter of approximately 4.0 mm. As a result of the frustoconical shape, the head 1112 has a minor diameter that increases in a proximal to distal direction. The major diameter remains constant, and as a result the thread surface area in contact with bone increases in a distal to proximal direction, enhancing the purchase of the screw into the bone.

The head 1112 further includes an angled surface 1134 (also "chamfer" or "bevel") and a driver recess 1136. The angled surface 1134 is formed between the top surface 1132 and the lateral surface 1122. The top surface 1132 has a width dimension that is greater than zero as measured along a diameter of the head, ensuring that the angled surface 1134 does not extend completely across the top of the screw 1110. In the instant example, the top surface 1132 has a width dimension of 0.42 mm, however the width dimension may be more or less depending upon the overall size of the bone screw 1110. By way of example, the angled surface 1134 may have a bevel angle $Ø_{12}$ within the range of 1-60° measured from the plane of the top surface 1132, which is generally perpendicular to the longitudinal axis $L_{12}$. By way of example, the bevel angle $Ø_{12}$ of the bone screw 1110 shown in FIGS. 37-39 is 50°. The angled surface 1134 is positioned generally parallel to and flush with an exterior surface of the bone forming part of the anatomical target site when the head is implanted during use to thereby reduce or eliminate a degree to which the head will extend beyond the exterior surface of the bone when the bone screw 1110 is implanted at an angle relative to the bone structure. The driver recess 1136 is formed into the top surface 1132 along the longitudinal axis $L_{12}$, and may have any shape suitable to receive a driver (e.g. flathead, Phillips-type, hexalobe, torx, etc.). By way of example, the helical thread 1124 of the present example has a 1.0 mm pitch.

By way of example, the shank 1114 is cylindrical in shape, and extends from a proximal end adjacent the neck 1116 to the distal end 1120 of the bone screw 1110. The shank 1114 comprises a curved lateral surface 1142 and a helical thread 1144 disposed around a distal portion of the curved lateral surface 1142. The shank further includes a proximally-positioned threadless section 1145 to enable compression.

By way of example, the threadless section 1145 may comprise approximately two-thirds of the length of the shaft with the distal one-third length being threaded. Other configurations are possible depending on the type and location of the fracture being treated. The shank 1114 may have a minor diameter within the range of 1.0 mm to 7.5 mm and a major diameter within the range of 1.5 mm to 8 mm. Preferably, the major diameter of the shank 1114 is less than the major diameter of the head 1112. In the example shown and described herein, the shank 1114 has a minor diameter of approximately 1.5 mm and a major diameter of approximately 2.5 mm. The helical thread 1144 may have a pitch 1146 within the range of 0.5 mm to 2.5 mm. By way of example, the helical thread 1144 of the present example has a 1.2 mm pitch. Since the pitch 1146 of the shank 1114 is neither the same as nor an even multiple (e.g. 2×) of the pitch 1138 of the head 1112, the bone screw 1110 is a compression screw. The shank 1114 further includes one or more cutting flutes 1148 disposed at the distal end 1120. The cutting flute 1148 acts to clear out bone material as the screw 1110 is driven into bone, which obviates the need for drilling a pilot hole during the surgical procedure.

The neck 1116 comprises a curved lateral surface 1150 that is tapered in the distal direction, to provide a smooth transition between the reverse conical head 1112 and the shank 1114.

The bone screw 1110 further includes a central lumen extending axially through the entirety of the screw 1110, identical to the central lumen shown and described above with respect to bone screw 1110. The central lumen is sized and configured to receive a guide wire (e.g. K-wire) therethrough to guide the bone screw 1110 to the correct implantation location.

Figure 40:
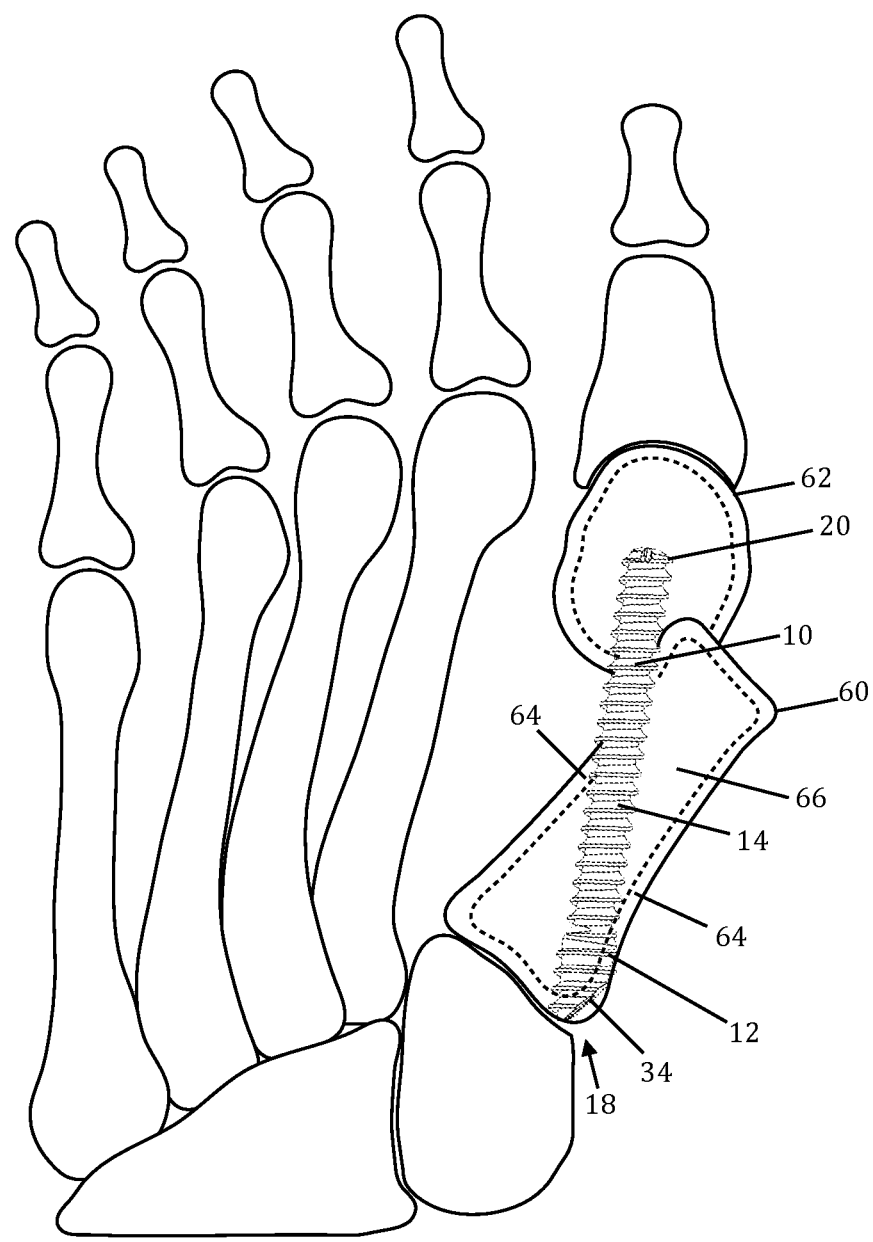
FIG. 40 is a plan view of a representative image of the bone screw of FIG. 1 in use during a bunion repair surgery, according to an embodiment of the disclosure.

The bone screw 10 and the various alternative examples described herein may be used in any number of orthopedic procedures in which at least two segments of bone need to be stabilized, for example in the case of a fracture. FIG. 40 illustrates one example of the bone screw 10 in use to stabilize first and second bone segments 60, 62 relative to one another, for example in the course of a bunion repair surgery. In the instant example, the bone screw 10 is inserted such that the proximal end 18 of the bone screw 10 engages the first bone segment 60 and the distal end 20 of the bone screw 10 engages the second bone segment 62. The bone screw 10 is positioned such that the head 12 and a portion of the shank 14 engage cortical bone 64 while passing through the cancellous bone 66 of one bone segment 60. The bone screw 10 is further positioned such that the beveled surface 34 is in alignment with the edge of bone, reducing/eliminating the portion of screw that would otherwise protrude from the bone. If compression-neutral screws are used, then the bone screw 10 holds the relative positioning of the bone segments without applying compressive force.

Figure 41:
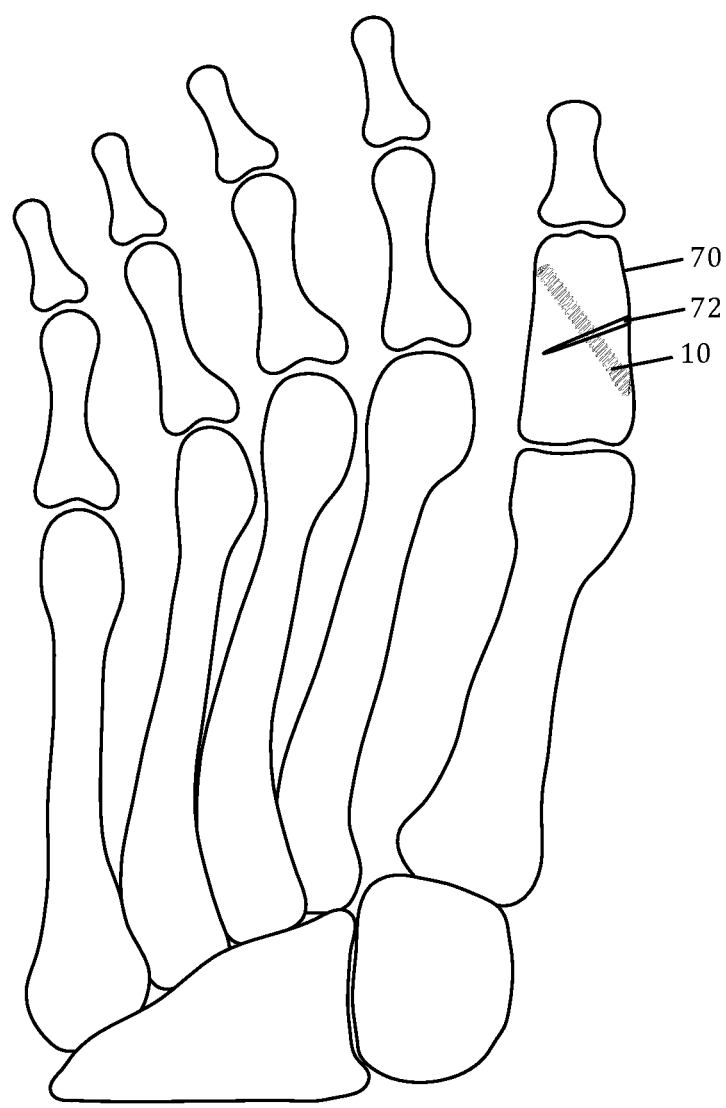
FIG. 41 is a plan view of a representative image of the bone screw of FIG. 1 in use to repair a fractured foot bone.
Figure 42:
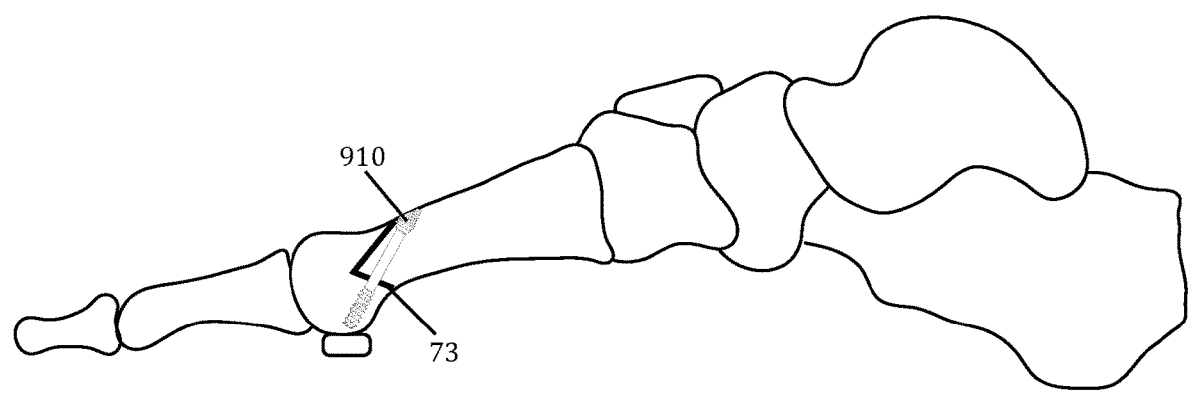
FIG. 42 is a plan view of a representative image of the bone screw of FIG. 31 in use during a bunion repair surgery, according to an embodiment of the disclosure.
Figure 43:
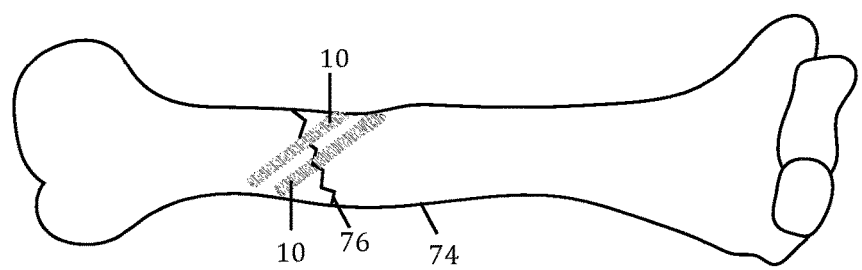
FIG. 43 is a perspective view of a representative image of multiple bone screws of FIG. 1 in use to repair a humus bone.
Figure 44:
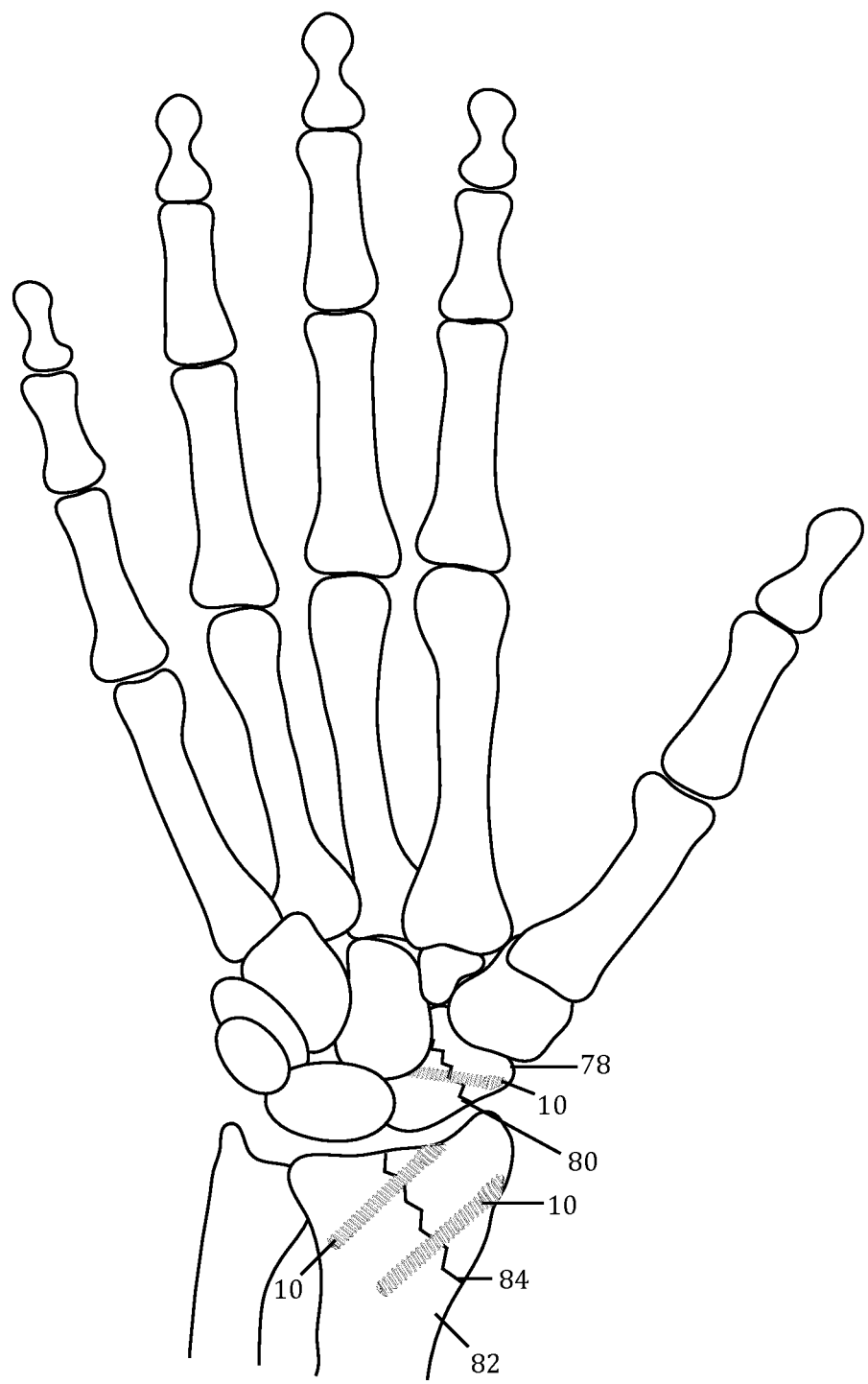
FIG. 44 is a plan view of a representative image of multiple bone screws of FIG. 1 in use to repair several fractures in a wrist.

The bone screw 10 may be provided in any number of size and length configurations to enable the bone screw 10 to be used to address a variety of indications. FIGS. 41-44 illustrate some example uses of the bone screw 10 described herein to stabilize fractures in several different bone locations. For example, FIG. 41 illustrates a bone screw 10 inserted into a phalange bone 70 in a foot to repair a fracture 72 or osteotomy. FIG. 42 illustrates a partially threaded bone screw 910 used to stabilize a V-shaped cut 73 during a distal metatarsal chevron osteotomy procedure for example to correct a bunion deformity. FIG. 43 illustrates a pair of bone screws 10 inserted into a humerus bone 74 to repair a fracture 76. FIG. 44 illustrates a plurality of bone screws 10 used to repair several fractures in the wrist area. For example, one bone screw 10 (e.g. a small bone screw 10) is inserted into a scaphoid bone 78 to repair fracture 80. A pair of bone screws 10 is inserted in to the radius bone 82 to repair fracture 84.

Figure 45:
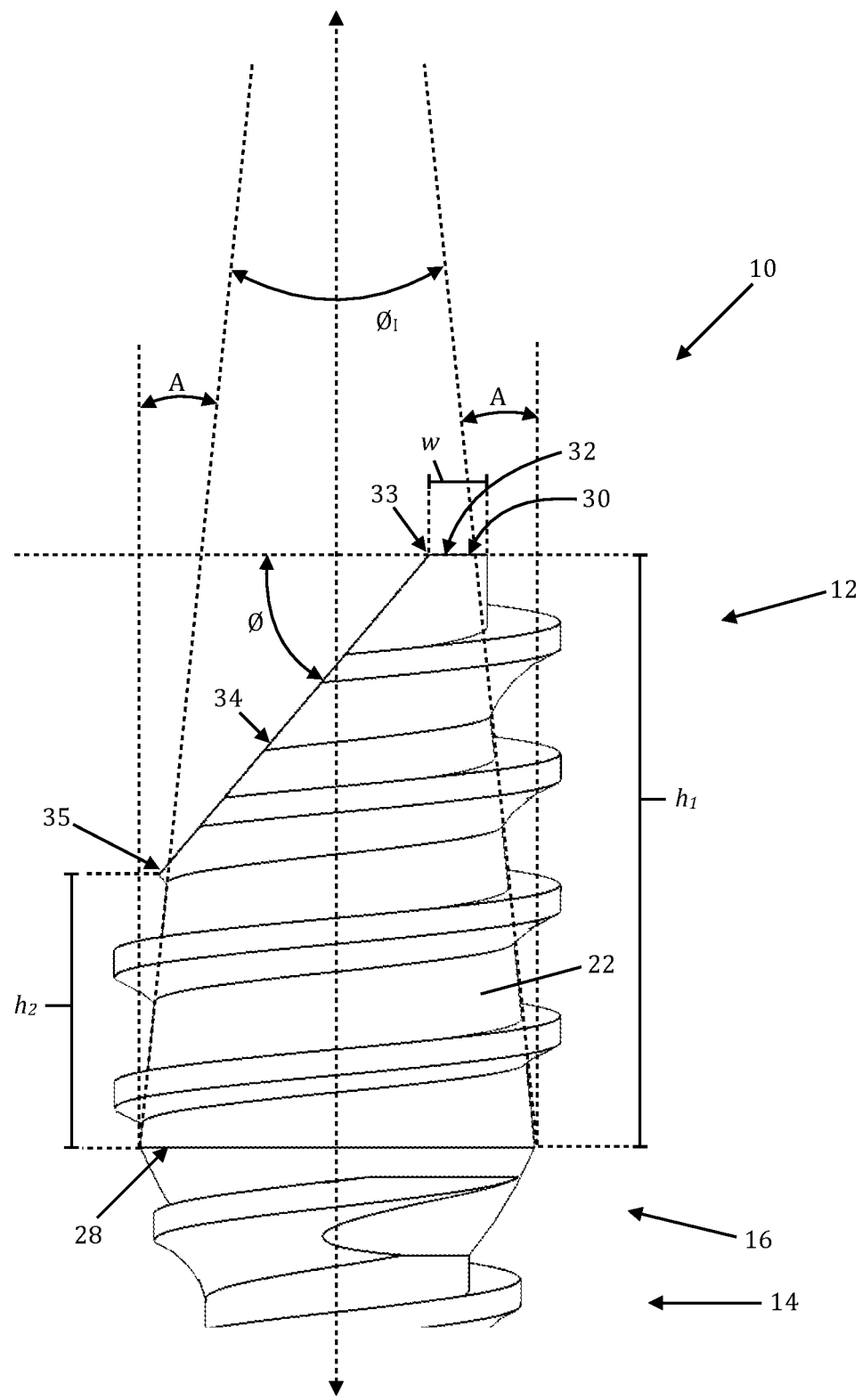
FIG. 45 is an enlarged plan view of the head region of the bone screw of FIG. 1.
Figure 46:
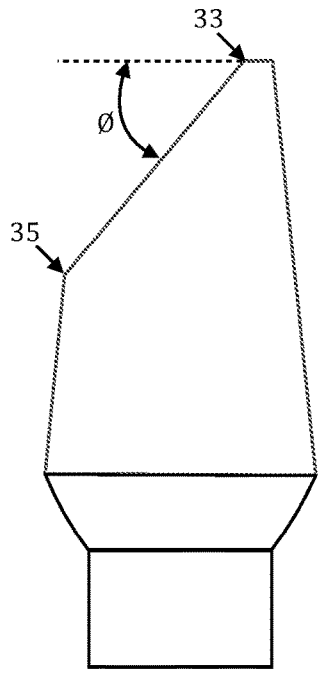
FIGS. 46-51 illustrate several examples of possible configurations of the head region of the bone screw of FIG. 1.
Figure 47:
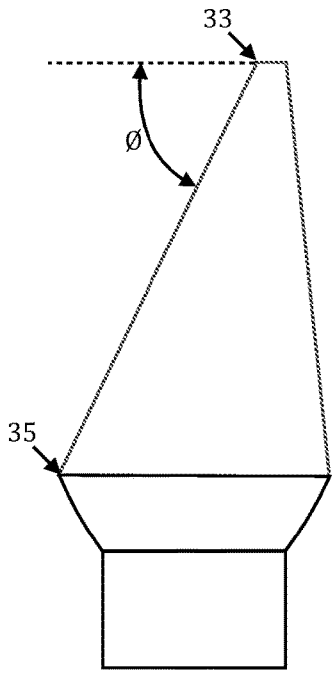
Figure 48:
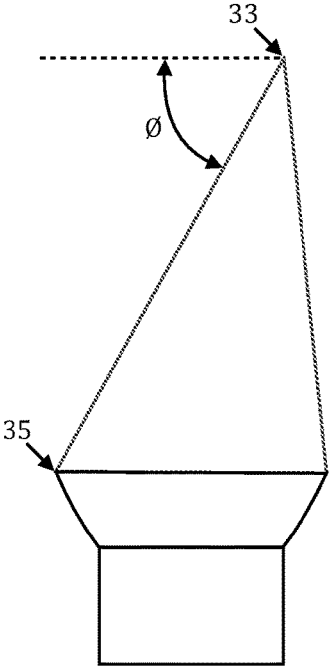
Figure 49:
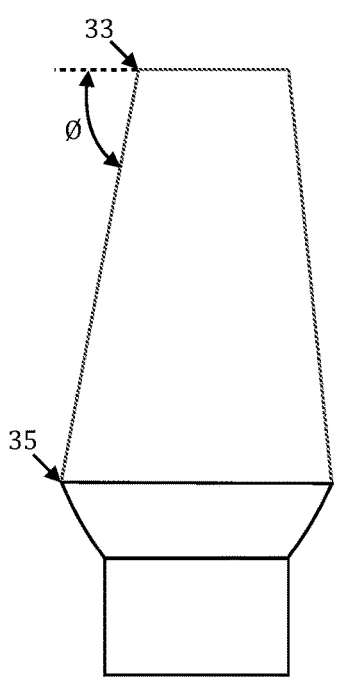
Figure 50:
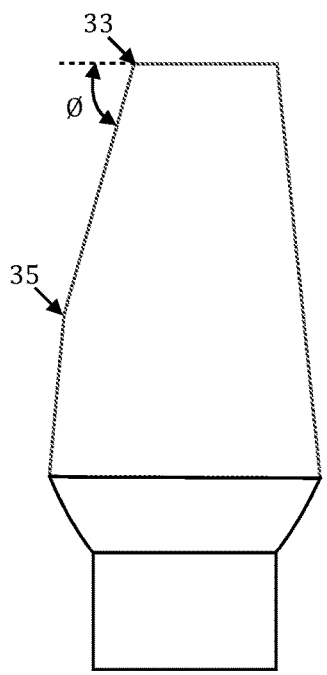
Figure 51:
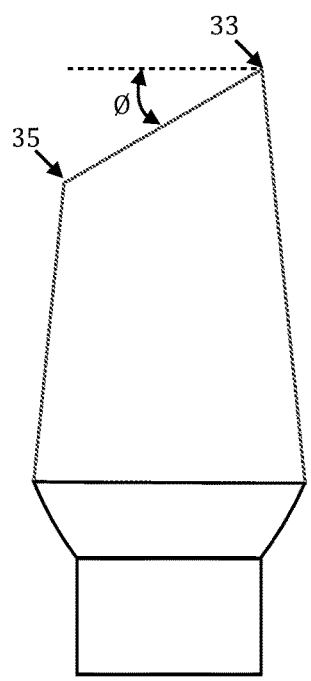

FIG. 45 is an enlarged view of the head 12 of the bone screw 10 described above with respect to FIGS. 1-6, illustrating in particular the various angles and surface dimensions of the head 12. Although shown and described with respect to head 12 of bone screw 10, the ensuing discussion may apply to any of the above examples without departing from the scope of the disclosure. As previously described, the head 12 is positioned at/near the proximal end 18 of the bone screw 10, and the shank 14 extends axially along a longitudinal axis L (also "vertical axis") from the neck 16 to the distal end 20 of the bone screw 10. The head 12 comprises a curved lateral surface 22 and a helical thread 24 disposed around the curved lateral surface 22. The head 12 has a generally frustoconical cross-sectional shape, wherein the wide base 28 of the frustum forms the distal-most border or base of the head 12, and the narrow base 30 of the frustum forms the proximal-most or top surface 32 of the bone screw 10. The curved lateral surface 22 is tapered in the proximal direction from the wide base 28 to the narrow base 30. By way of example, the curved lateral surface 22 is tapered at an angle A of 5.9° relative to the longitudinal axis L (or a axis parallel to the longitudinal axis) resulting in the cone defining the shape of the head having an included angle $Ø_I$ of 11.8°. The angle A may be within the range of 5-15° (and therefore the included angle $Ø_I$ may be within the range of 10-30°) without departing from the scope of the disclosure.

In the instant example, the head 12 is beveled, in that it further includes an angled surface 34 (also "chamfer" or "bevel") that functions to reduce/eliminate the amount of screw material that may extend beyond the edge of a bone structure when the bone screw 10 is implanted at an angle relative to the bone structure. The angled surface 34 is formed between the top surface 32 and the lateral surface 22. Because of the angled surface 34, the head 12 has a major height dimension $h_1$ defined as the vertical distance between the base of the head (e.g. the wide base 28 of the frustum) and the top surface 32 (e.g. the narrow base 30 of the frustum), and a minor height dimension $h_2$ defined as the vertical distance between the base of the head and the distal-most intersection 35 between the angled surface 34 and lateral surface 22.

The top surface 32 has a width dimension w that is defined by the greatest distance between the proximal-most edge of the lateral surface 22 and the proximal-most edge 33 of the angled surface 34. In most example embodiments, the width dimension w is greater than zero (e.g. w>0), ensuring that the angled surface 34 does not extend completely across the top of the screw 10. In some instances, the width dimension w may be equal to zero (e.g. w=0), in which case the proximal-most edge 33 of the angled surface 34 intersects the proximal-most edge of the lateral surface 22. In the instant example, the top surface 32 has a width dimension of 0.65 mm, however the width dimension may be more or less depending upon the overall size of the bone screw 10 and the angle Ø of the bevel. By way of example, the angled surface 34 may have a bevel angle Ø wherein 0°<Ø<85° measured from the plane of the top surface 32, which is generally perpendicular to the longitudinal axis L. By way of example, the bevel angle Ø of the bone screw 10 shown in FIG. 38 is 50°.

FIGS. 46-51 illustrate several examples of possible configurations of the head 12 that are created by varying the position of the proximal-most edge 33 of the angled surface 34 and the distal-most intersection 35 between the angled surface 34 and lateral surface 22, and how their relative positions alters the bevel angle Ø and the width dimension w of the top surface 32. For example, FIG. 40 depicts an example of a head 12 wherein w>0 and $h_2$>0. In this example, the bevel angle Ø is approximately 50°. FIG. 41 depicts an example of a head 12 wherein w>0 and $h_2$ =0. In this example, the bevel angle Ø is approximately 65.5°. FIG. 42 depicts an example of a head 12 wherein w=0 and $h_2$=0. In this example, the bevel angle Ø is approximately 61.2°. FIG. 43 depicts an example of a head 12 wherein w>0 and $h_2$=0. In this example, the bevel angle Ø is approximately 79.5°. FIG. 44 depicts another example of a head 12 wherein w>0 and $h_2$>0. In this example, the bevel angle Ø is approximately 74.5°. FIG. 45 depicts an example of a head 12 wherein w=0 and $h_2$>0. In this example, the bevel angle Ø is approximately 30°. In this manner, bone screws of the present disclosure may be provided with chamfers of various angles depending upon the need of the surgeon for the particular surgery performed (e.g. insertion angles, etc.).

It is important to note that any element or feature shown and described herein with respect to any particular example may be used in combination with any other feature(s) or element(s) shown and described with respect to other examples without limitation.

What is claimed is:

1. A screw for orthopedic surgery at an anatomical target site in a human patient, comprising:
    a head, a shank, and a neck extending between said head and said shank, wherein said head, neck and shank are colinear along a longitudinal axis extending between a proximal end of said head and a distal end of said shank;
    said head including:
        a reverse frustoconical cross-sectional shape defined by a narrow base at said proximal end of said head, a wide base at a distal end of said head, a minor diameter that increases from said narrow base to said wide base, and a curved lateral surface extending between said narrow base and said wide base that is tapered relative to said longitudinal axis to define at a reverse taper angle;
        at least one helical thread extending clockwise in a direction from said narrow base of said head to said wide base of said head, said at least one helical thread having a thread surface area and a diameter that defines a major diameter of said head, wherein said major diameter at least one of increases and remains constant from said wide base to said narrow base to increase said thread surface area in a distal to proximal direction, said thread surface area configured to contact a bone forming part of said anatomical target site when said head is implanted during use to thereby enhance the purchase of said head into said bone, said at least one helical thread having at least one pitch;
        a beveled surface extending from said narrow base of said head to a predetermined location along said curve lateral surface, wherein said beveled surface is angled relative to an upper surface of said head that is perpendicular to said longitudinal axis to define a bevel angle dimensioned such that said beveled surface may be positioned generally parallel to and flush with an exterior surface of a bone forming part of said anatomical target site when said head is implanted during use to thereby reduce or eliminate a degree to which said head will extend beyond said exterior surface of said bone when said head is implanted at an angle relative to said bone; and
        a drive feature dimensioned to cooperate with an instrument such that said head, shank, and neck may be rotated about said longitudinal axis in order to drive said shank, neck and head into an anatomical target of a patient; and
    said shank including:
        a curved lateral surface having at least one helical thread extending clockwise in a direction from a proximal end of said shank towards said distal end of said shank, said at least one helical thread having a diameter that defines a major diameter of said shank that is less than a minimum value of said major diameter of said head, and said at least one helical thread including at least one pitch.

2. The screw for orthopedic surgery of claim 1, wherein said reverse taper angle of said head is between approximately 5 and 15 degrees.

3. The screw for orthopedic surgery of claim 2, wherein said reverse taper angle of said head is approximately 6 degrees.

4. The screw for orthopedic surgery of claim 1, wherein said pitch of said at least one helical thread of said head is in the range of 0.5 mm to 2.5 mm.

5. The screw for orthopedic surgery of claim 4, wherein said pitch of said at least one helical thread of said head is approximate 1.5 mm.

6. The screw for orthopedic surgery of claim 1, wherein said pitch of said at least one helical thread of said head is approximately equal to the pitch of said at least one helical thread of said shank such that said screw is a compression neutral screw in use.

7. The screw for orthopedic surgery of claim 1, wherein said pitch of said at least one helical thread of said head is at least one of: (a) not approximately equal to the pitch of said at least one helical thread of said shank such that said screw is a compression screw in use; and (b) of varying pitch including a first pitch at said narrow base and a second pitch at said wide base such that said screw is a compression screw in use.

8. The screw for orthopedic surgery of claim 1, wherein said bevel angle of said head is in the range of between 1 and 60 degrees.

9. The screw for orthopedic surgery of claim 8, wherein said bevel angle of said head is approximately 50 degrees.

10. The screw for orthopedic surgery of claim 1, wherein said minor diameter of said head is within the range of 1.75 mm to 9 mm.

11. The screw for orthopedic surgery of claim 10, wherein said minor diameter of said head is approximately 4.5 mm at said wide base.

12. The screw for orthopedic surgery of claim 1, wherein said major diameter of said head is in the range of 2 mm to 10 mm.

13. The screw for orthopedic surgery of claim 12, wherein said major diameter of said head is approximately 5 mm.

14. The screw for orthopedic surgery of claim 1, wherein said shank has a minor diameter in the range of between 1.0 mm and 7.5 mm.

15. The screw for orthopedic surgery of claim 14, wherein said minor diameter of said shank is approximately 3 mm.

16. The screw for orthopedic surgery of claim 1, wherein said major diameter of said shank is in the range of between 1.5 mm to 8 mm.

17. The screw for orthopedic surgery of claim 16, wherein said major diameter of said shank is approximately 4 mm.

18. The screw for orthopedic surgery of claim 1, wherein at least one of said at least one helical thread of said head includes at least one of a cutting flute and a reverse cutting flute.

19. The screw for orthopedic surgery of claim 1, wherein said at least one of said at least one helical thread of said shank includes a cutting flute.

20. The screw for orthopedic surgery of claim 1, wherein said at least one helical thread of said shank is a dual helix screw thread.

* * * * *